(12) United States Patent
Lee et al.

(10) Patent No.: US 10,172,554 B2
(45) Date of Patent: Jan. 8, 2019

(54) CLOTHING WITH MINIMIZED MOTION ARTIFACT HAVING TEXTILE ELECTRODE KIT MOUNTED THERETO

(71) Applicants: Industry-Academic Cooperation Foundation, Yonsei University, Seoul (KR); Konkuk University Industrial Cooperation Corp., Seoul (KR)

(72) Inventors: Joo Hyeon Lee, Seoul (KR); Jeong-Whan Lee, Gyeonggi-do (KR); Young-Jae Lee, Gyeonggi-do (KR); Hye Ran Koo, Seoul (KR)

(73) Assignees: Industry-Academic Cooperation Foundation, Yonsei University, Seoul (KR); Konkuk University Industrial Cooperation Corp., Seoul (KR)

( * ) Notice: Subject to any disclaimer, the term of this patent is extended or adjusted under 35 U.S.C. 154(b) by 1011 days.

(21) Appl. No.: 14/478,701

(22) Filed: Sep. 5, 2014

(65) Prior Publication Data

US 2015/0065842 A1 Mar. 5, 2015

(30) Foreign Application Priority Data

Sep. 5, 2013 (KR) .......................... 10-2013-0106380

(51) Int. Cl.
*A61B 5/00* (2006.01)
*A61B 5/0408* (2006.01)
(Continued)

(52) U.S. Cl.
CPC ........ *A61B 5/6804* (2013.01); *A61B 5/04085* (2013.01); *A61B 5/053* (2013.01); *A61B 5/6823* (2013.01); *A61B 5/0492* (2013.01)

(58) Field of Classification Search
CPC ... A61B 5/6804; A61B 5/6805; A61B 21/065; A61N 1/0484; A41B 1/00; A41B 1/02; A41B 1/04; A41B 1/08; A41B 1/12; A41B 1/18; A41B 1/20; A41B 1/22; A41B 7/00; A41B 7/001; A41B 7/006; A41D 5/00
(Continued)

(56) References Cited

U.S. PATENT DOCUMENTS

| 4,635,301 A * | 1/1987 | Sulser ...................... A41B 1/00 2/105 |
| 2008/0218180 A1* | 9/2008 | Waffenschmidt ...... A61B 5/053 324/633 |

(Continued)

FOREIGN PATENT DOCUMENTS

| KR | 100863064 | 10/2008 |
| KR | 101302600 | 8/2013 |

*Primary Examiner* — Eunhwa Kim

(57) ABSTRACT

A textile electrode kit mounted to the clothing includes a contact-type electrode or a non-contact electrode, and the textile electrode kit may be mounted to a clothing having a lower fixed member configured to reduce a motion artifact and a partially three-dimensional clothing structure by means of sewing. On occasions, the textile electrode kit having a non-contact electrode may be inserted into and used in an electrode-mounting pocket or an electrode-mounting tunnel formed at the clothing. The textile electrode kit of the present disclosure may detect various kinds of bio signals such as a heart activity signal, an electrocardiogram (ECG) signal, an electromyogram signal, a breathing signal or the like.

8 Claims, 19 Drawing Sheets

(51) Int. Cl.
*A61B 5/053* (2006.01)
*A61B 5/0492* (2006.01)

(58) Field of Classification Search
USPC .......................................... 600/388, 389, 390
See application file for complete search history.

(56) References Cited

U.S. PATENT DOCUMENTS

| | | | |
|---|---|---|---|
| 2010/0185076 A1* | 7/2010 | Jeong | A61B 5/0408 600/388 |
| 2012/0102618 A1* | 5/2012 | Burmeister | A41B 1/08 2/122 |
| 2012/0144551 A1* | 6/2012 | Guldalian | A61B 5/04085 2/102 |
| 2014/0206976 A1* | 7/2014 | Thompson | A61B 5/0006 600/391 |
| 2014/0336493 A1* | 11/2014 | Kulach | A61B 5/04085 600/390 |

* cited by examiner (a)

(b)

(a)  (b)

CLOTHING WITH MINIMIZED MOTION ARTIFACT HAVING TEXTILE ELECTRODE KIT MOUNTED THERETO

CROSS-REFERENCE TO RELATED APPLICATIONS

This application claims priority under 35 U.S.C. § 119 to Korean Patent Application No, 10-2013-0106380 filed on Sep. 5, 2013 in the Korean Intellectual Property Office, the disclosure of which is incorporated herein by reference in its entirety.

TECHNICAL FIELD

The following disclosure relates to clothing with a minimized motion artifact to which a textile electrode kit is mounted, which includes a textile electrode kit having a conductive textile-based bio signal measurement sensor, and a clothing structure configured to stably detect a bio signal such as a heart activity signal and an electrocardiogram (ECG) of a subject person in a non-restrictive and non-invasive way with a minimized motion artifact during ordinary activities by mounting the textile electrode kit to the clothing.

BACKGROUND

A patient suffering from a chronic disease such as a cardiac disease should monitor his/her health state, and for this, the patient should directly visit a hospital inconveniently with great costs.

In case of existing sensors, accuracy of heart activity signal measurement deteriorates if a contact point between an electrode and a human body deviates due to a motion of a user. In addition, such existing sensors are inconvenient since they should be mounted to excessively press a human body for a long time. These sensors are not suitable for continuous measurement at daily life.

Korean Patent Registration No. 10-0863064 or the like proposes a bio-signal measurement clothing to which an electrode is mounted. This clothing includes at least one electrode integrally coupled to the inner side of the clothing and coming into contact with the skin surface to detect a bio signal. However, if a human body moves while the electrode integrated with the clothing is detecting a bio signal in contact with the human body, a signal with much motion artifact is detected, which deteriorates accuracy and precision in analysis of the detected bio signal. In other words, even though bio signal may be detected non-restrictively, non-Invasively and continuously by using the existing clothing integrated with an electrode, since a gap is inevitably present between the electrode and the human body due to bent portions of the human body, if the human body moves, the electrode moves accordingly and thus the motion artifact increases as much due to the gap.

Therefore, there is needed clothing with a minimized motion artifact to which a textile electrode kit is mounted, which may measure a bio signal through clothing in a non-restrictive, non-invasive and continuous way anytime and anywhere while minimizing a measurement artifact caused by a motion of the user.

In the textile electrode kit of the present disclosure, a non-contact electrode as well as a contact-type electrode, which has been widely used in the art from the past, is used.

In the present disclosure, as a non-contact electrode, a coil-type magnetic induction sensor is used. In relation to the coil-type magnetic induction sensor, the inventors of the present disclosure have a patent right for Korean Patent Registration No. 10-1302600 which is directed to a conductive textile-based bio signal measurement sensor.

FIG. 1 is a diagram for illustrating a configuration for detecting a volume change according to a change of inductance by using the conductive textile-based bio-signal measurement sensor disclosed in Korean Patent Registration No. 10-1302600.

An inductor-type bio-signal measurement sensor 40 is mounted, and a signal detector 30 is mounted to an outer side of the inductor-type bio-signal measurement sensor. The detector includes an oscillating unit 50 and a demodulating unit 70.

The oscillating unit 50 is composed of an oscillation circuit having L and C to transmit a vibration signal to the inductor-type bio-signal measurement sensor 40.

The inductor-type bio-signal measurement sensor 40 is configured to maximize sensitivity by disposing a ferromagnetic substance core capable of focusing a magnetic flux on a center portion of the coil. In other words, a volume of interest (VOI) may cause a temporal variation, formed by a geometric structure of a coil sensor, namely influenced by a magnetic force, and the conductive textile-based bio-signal measurement sensor 40 senses a change of eddy current caused by electric conductivity of a substance located in the volume.

If the inductor-type bio-signal measurement sensor 40 receives a vibration signal, a magnetic field of a time-varying function is formed in a living body in the volume of interest (VOI) 20, and the generated magnetic field creates an eddy current in the substance. The inductance of the sensor is influenced by a movement of a detection target. Therefore, a vibration signal of the heart muscle causes a change of inductance of the coil, and this signal is transmitted through the oscillating unit 50 to the demodulating unit 70.

The demodulating unit 70 removes a vibration signal applied to the inductor-type bio signal measurement sensor 40 from the above signal to detect only a bio signal.

In detail, a magnetic field is formed by a current minutely flowing on the coil of the inductor-type bio-signal measurement sensor 40. The magnetic field varying according to time induces an eddy current in a detection target (or, in a human body), and the formed induced current generates a minute magnetic field in a direction opposite to the magnetic field formed at the coil. The change of the magnetic field of the coil of the inductor-type bio-signal measurement sensor 40 results in a variation of the inductance (the induced magnetic field) of the coil. To detect the variation, the oscillating unit 50 serving as an oscillation circuit is provided to regard the coil of the inductor-type bio-signal measurement sensor 40 as an inductor circuit, and in this case, a frequency modulation representing a variation of a frequency of an oscillator exhibited due to a movement of a detection target (in a human body). As one of detection methods, the demodulating unit 70 may trace a modulated frequency by using a phase-locked loop (PLL). If this frequency demodulation is used, a movement of the detection target is exhibited as a PLL output, which allows a movement of the heart to be measured.

SUMMARY

An embodiment of the present disclosure is directed to providing clothing with a minimized motion artifact to which a textile electrode kit is mounted, which includes a textile electrode kit composed of a conductive textile-based bio signal measurement sensor or the like, and a clothing structure configured to stably detect a bio signal such as a heart activity signal and an electrocardiogram (ECG) of a subject person in a non-restrictive and non-invasive way with a minimized motion artifact during ordinary activities by mounting the textile electrode kit to the clothing.

Another embodiment of the present disclosure is directed to providing clothing with a minimized motion artifact to which a textile electrode kit is mounted, in which the textile electrode kit mounted to the clothing is composed of a contact-type bio-signal measurement sensor and attached to the clothing by using a sewing thread, other materials or subsidiary materials.

Another embodiment of the present disclosure is directed to providing clothing with a minimized motion artifact to which a textile electrode kit is mounted, in which when the textile electrode kit mounted to the clothing is a non-contact bio-signal measurement sensor, the textile electrode kit is attached to the clothing by means of a sewing thread, other materials or subsidiary materials or is inserted into a tunnel provided at a clothing body part.

Another embodiment of the present disclosure is directed to providing clothing with a minimized motion artifact to which a textile electrode kit is mounted, in which the textile electrode kit is mounted to the clothing with a partially three-dimensional clothing structure so that the textile electrode is closely adhered to bent portions of a human body.

Another embodiment of the present disclosure is directed to providing clothing with a minimized motion artifact to which a textile electrode kit mounted, in which the textile electrode kit is mounted to the clothing using a design element such as a sleeve structure or a neckline structure which does not give an influence on stable detection of a bio signal during daily life.

In an aspect of the present disclosure, there is provided clothing to which a textile electrode kit for detecting a bio signal is mounted, which includes: elastic members respectively located below right and left under-armpits or right and left chests and made of an elastic material; a front center band made of an non-elastic material with a band shape and located at a front sheet of the clothing, one end of the front center band being mounted to one end of the left elastic member, the other end of the front center band being mounted to one end of the right elastic member; a back center band made of an non-elastic material with a band shape and located at a rear sheet of the clothing, one end of the back center band being mounted to the other end of the left elastic member, the other end of the back center band being mounted to the other end of the right elastic member; and a back lower central dart vertically extending from a center of a lower end of the back center band to a waist portion.

In addition, the clothing according to an embodiment of the present disclosure may further include: a chest center elastic member located at a center of the front center band and made of an elastic material; a left front center band made of an non-elastic material, one end of the left front center band being mounted to one end of the left elastic member, the other end of the left front center band being mounted to one end of the chest center elastic member; and a right front center band made of an non-elastic material, one end of the right front center band being mounted to one end of the right elastic member, the other end of the right front center band being mounted to the other end of the chest center elastic member.

In addition, the clothing according to an embodiment of the present disclosure may further include a front upper central dart vertically extending from a neckline center of the front sheet to a lower end of the chest center elastic member.

In addition, the clothing according to an embodiment of the present disclosure may further include at least one of: a first vertical support unit made of an non-elastic material with a band shape and vertically mounted from an intermediate portion between a neckline center of the front sheet and a point where the neckline meets a shoulder line to an upper portion of the front center band; and a second vertical support unit made of an non-elastic material with a band shape and vertically mounted from an intermediate portion between a lower center of the front center band and one end or the other end of the front center band to a lower end of the front sheet.

In addition, the clothing according to an embodiment of the present disclosure may further include: a waste sideline elastic members located at right and left side seams of a waist portion and made of an elastic material; a front abdominal band made of an non-elastic material with a band shape and located at the front sheet, one end of the front abdominal band being mounted to one end of the left waste sideline elastic member, the other end of the front abdominal band being mounted to one end of the right waste sideline elastic member; and a back abdominal band made of an non-elastic material with a band shape and located at the rear sheet, one end of the back abdominal band made being mounted to the other end of the left waste sideline elastic member, the other end of the back abdominal band being mounted to the other end of the right waste sideline elastic member.

In addition, in the clothing according to an embodiment of the present disclosure, a textile electrode kit may be mounted to the front center band or the back center band.

In addition, in the clothing according to an embodiment of the present disclosure, a textile electrode kit may be mounted to the front center band, the back center band, the front abdominal band or the back abdominal band.

In addition, in the clothing according to an embodiment of the present disclosure, at least one of the front center band and the back center band may be disposed at an inner side of the clothing which comes into contact with the skin.

In addition, in the clothing according to an embodiment of the present disclosure, a sleeve portion connecting the shoulder and the arm of the clothing may be formed with a mesh structure, a slit structure, a cut-out structure, a folding structure or a pleat structure.

In addition, in the clothing according to an embodiment of the present disclosure, a neck girth of the clothing may be formed with a mesh structure, a slit structure, a cut-out structure, a folding structure or a pleat structure.

In addition, in the clothing according to an embodiment of the present disclosure, the textile electrode kit may include: an electrode having a surface electrode and coming into contact with the skin to detect a bio signal; a lower fixed member having one surface to which the electrode is mounted; a three-dimensional structure mounted to the other surface of the lower fixed member; a signal detection module located on the three-dimensional structure and mounted in a housing to amplify the bio signal received from the electrode and remove artifact therefrom; and an upper cover member configured to surround the signal detection module and having a rim which is sewed or attached together with a rim of the lower fixed member.

In addition, in the clothing according to an embodiment of the present disclosure, the textile electrode kit may include: an electrode having a spiral coil formed on a con-mounted textile sheet to receive an oscillation signal from an oscillation circuit and output the oscillation signal including the bio signal; a three-dimensional structure located on the electrode; a signal detection module located on the three-dimensional structure and mounted in a housing, the signal detection module including an electrode driving unit which has the oscillation circuit to output the oscillation signal, the signal detection module detecting the bio signal from the oscillation signal which is received from the electrode and includes the bio signal, the signal detection module amplifying the detected bio signal and removing artifact therefrom; and an upper cover member configured to surround the signal detection module and having a rim which is sewed or attached together with a rim of the coil-mounted textile sheet or sewed or attached together with of a lower fixed member located below the electrode.

In addition, in the clothing according to an embodiment of the present disclosure, the textile electrode kit may include: an electrode having a spiral coil formed on a coil-mounted textile sheet to receive an oscillation signal from an oscillation circuit and output the oscillation signal including the bio signal; a three-dimensional structure located above a lower fixed member and below the electrode; and an upper cover member configured to surround the electrode and having a rim which is sewed or attached together with a rim of the lower fixed member.

In addition, in the clothing according to an embodiment of the present disclosure, the textile electrode kit may include: an electrode having a spiral coil formed on a coil-mounted textile sheet to receive an oscillation signal from an oscillation circuit and output the oscillation signal including the bio signal; a three-dimensional structure located below the electrode; and a lower fixed member having one surface to which the three-dimensional structure is mounted, the lower fixed member having a rim which is sewed together with a rim of the coil-mounted textile sheet.

In addition, in the clothing according to an embodiment of the present disclosure, upper and lower portions of two textiles may be sewed to form an electrode-mounting tunnel having right and left openings, and the textile electrode kit may be installed in the electrode-mounting tunnel.

If the clothing with a minimized motion artifact to which a textile electrode kit is mounted according to the present disclosure is used, the textile electrode kit is composed of a conductive textile-based bio signal measurement sensor or the like to detect a bio signal in a non-restrictive way, and a clothing structure is configured to stably detect a bio signal such as a heart activity signal and an electrocardiogram (ECG) of a subject person in a non-restrictive and on-invasive way with a minimized motion artifact during ordinary activities by mounting the textile electrode kit to the clothing, thereby allowing stable signal detection with enhanced accuracy in a non-restrictive and non-invasive way.

In addition, in the present disclosure, if the textile electrode kit mounted to the clothing is a contact-type bio-signal measurement sensor, the textile electrode kit is attached to the clothing by using a sewing thread as well as a specific clothing structure, thereby minimizing a motion artifact in the detected signal.

In addition, in the present disclosure, if the textile electrode kit mounted to the clothing is a non-contact bio-signal measurement sensor, the textile electrode kit is attached to the clothing by means of a sewing thread as well as a specific clothing structure or is inserted into a tunnel provided at a clothing body part. In addition, a non-contact bio-signal measurement sensor such as a con-type magnetic induction sensor is used to detect a signal in a non-restrictive and non-invasive, thereby allowing detection of a signal with a minimized motion artifact.

In addition, in the present disclosure, the textile electrode kit is mounted to the clothing with a partially three-dimensional clothing structure for minimizing a motion artifact so that the textile electrode is closely adhered to bent portions of a human body, thereby ensuring a wearing comfort and easy activities and allowing detection of a signal with a minimized motion artifact.

DETAILED DESCRIPTION OF EMBODIMENTS

Hereinafter, clothing with a minimized motion artifact to which a textile electrode kit is mounted according to the present disclosure will be described in detail with reference to the accompanying drawings.

In the present disclosure, the textile electrode kit mounted to the clothing includes a contact-type electrode or a non-contact electrode, and the textile electrode kit may be mounted to a clothing having a lower fixed member configured to reduce a motion artifact and a partially three-dimensional clothing structure by means of sewing. On occasions, the textile electrode kit having a non-contact electrode may be inserted into and used in an electrode-mounting pocket or an electrode-mounting tunnel formed at the clothing. The textile electrode kit of the present disclosure may detect various kinds of bio signals such as a heart activity signal, an electrocardiogram (ECG) signal, an electromyogram signal, a breathing signal or the like.

Figure 1:
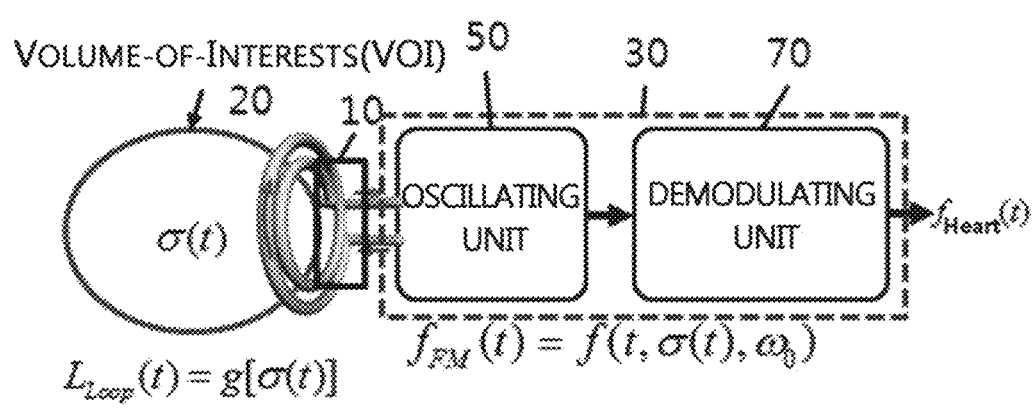
FIG. 1 is a diagram for illustrating the concept of a conductive textile-based bio signal measurement sensor disclosed in Korean Patent Application No. 10-2012-0092695.
Figure 2A:
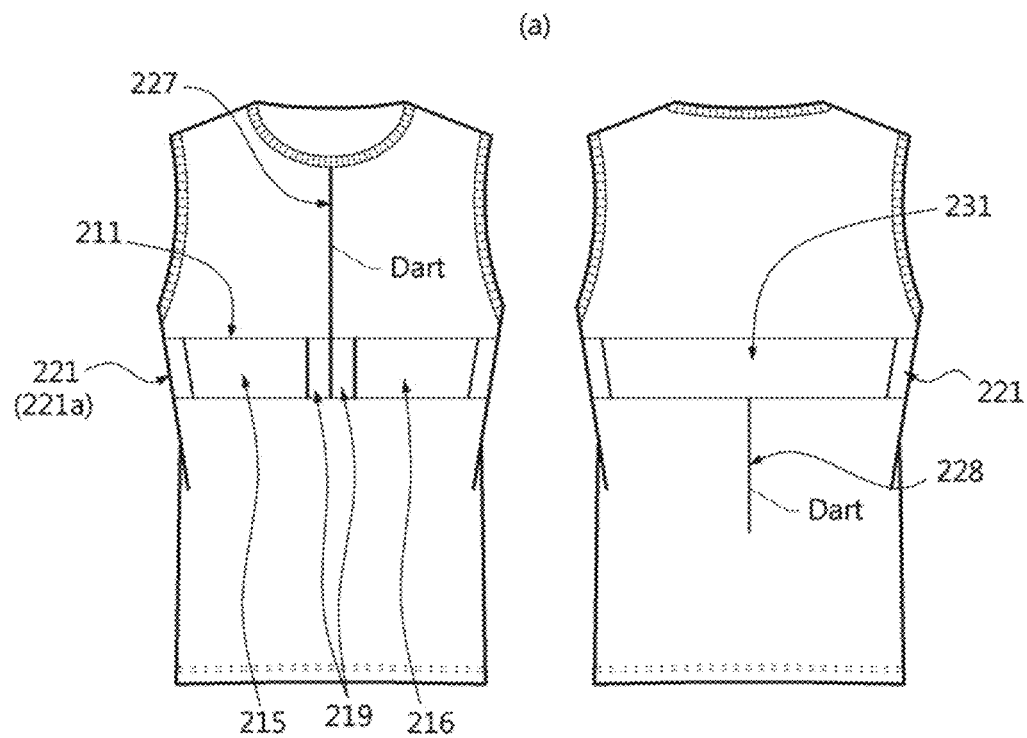
FIG. 2a shows a structure of clothing with a minimized motion artifact, to which a textile electrode kit is mounted according to a first embodiment of the present disclosure.
Figure 2A:
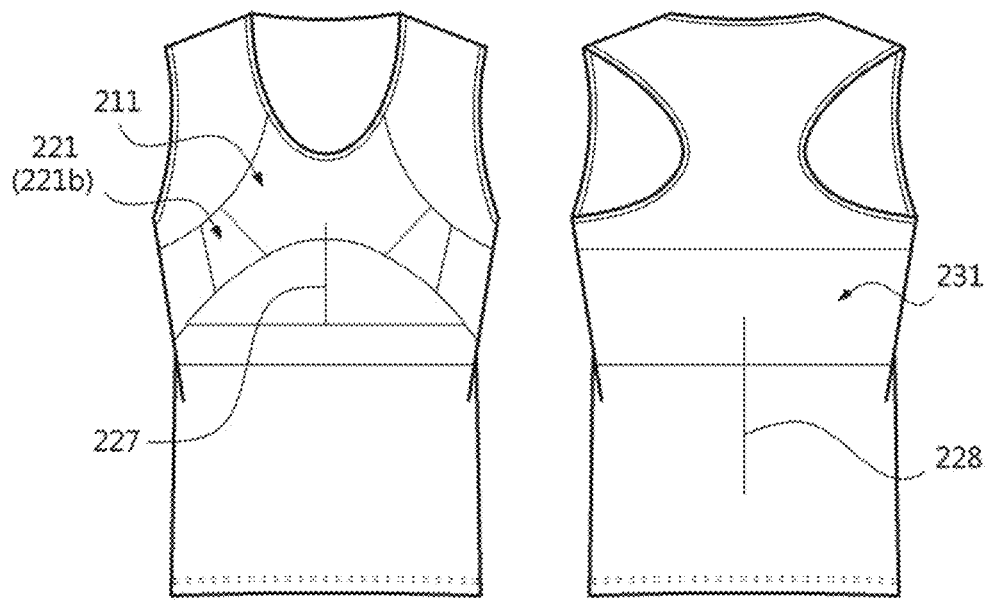

FIG. 2a shows a structure of clothing with a minimized motion artifact, to which a textile electrode kit is mounted according to a first embodiment of the present disclosure.

In FIG. 2a, a front center band 211 and a back center band 231 are connected through right and left elastic members 221. The front center band 211 has a chest center elastic member 219 at a center portion, a left front center band 215 at a left side of the chest center elastic member 219, and a right front center band 216 at a right side of the chest center elastic member 219. A front upper central dart 227 which is a vertical cut line formed from a neckline center of a front sheet to a lower end of the front center band 211, namely a lower end of the chest center elastic member 219, is provided, and a back lower central dart 228 which is a vertical cut line formed from a center of the lower end of the back center band 231 to the waist portion is provided. On occasions, a rear upper center dart (not shown) may also be provided at an upper portion of the rear sheet, similar to the front upper central dart 227.

The elastic member 221 is located below right and left armpits or right and left chests, connects the front center band 211 to the back center band 231, and is made of an elastic material. For this reason, even though the front center band 211 and the back center band 231 made of non-elastic material are provided at the front and rear sheets, easier motion may be ensured.

In the present disclosure, the elastic material means a material with good elasticity, opposite to an non-elastic property, for example a knitted textile containing at least 3% of polyurethane (spandex), a knitted fabric such as rib organization or accordion organization, an embroidered fabric containing at least 5% of elastic thread, an elastic band, rubber bands with various widths, smocking or the like.

The elastic member 221 may be an under-armpit elastic member 221a disposed below the right and left armpits as shown in Portion (a) of FIG. 2a or an under-chest elastic member 221b disposed below the right and left chests as shown in (b) of FIG. 2a. The elastic member 211 is made of highly-stretchable material or elastic material.

The under-armpit elastic member 221a may have a width (vertical) of at least 5 cm to 10 cm and a breadth (horizontal) of ⅛ of a minimum chest size to ¼ of a maximum chest size, and the breadth and width (vertical) of the under-armpit elastic member 221a may vary depending on the material.

The under-armpit elastic member 221a is located at a point where a bust line crosses with a side seam.

The under-chest elastic member 221b may be particularly disposed below both breasts of a woman, for clothing of a woman. This under-chest elastic member 221b is disposed between the side seams and the center of breasts and is located in consideration of a body type of a wearer. At this time, a neckline of the woman clothing may have a halter structure.

The front center band 211 crosses the chest portion at the front sheet and is connected from a lower portion of the left armpit to a lower portion of the right armpit with a band shape. In case of a woman clothing, the front center band 211 may extend to the neckline so as to be disposed above the breasts.

A left front center band 215, a right front center band 216 and a chest center elastic member 219 are provided.

One of the left front center band 215 is mounted to the left elastic member 221, and the other end is mounted to one end of the chest center elastic member 219 through a lower portion of the left chest.

One end of the right front center band 216 is mounted to the right elastic member 221, and the other end is mounted to the other end of the chest center elastic member 219 through a lower portion of the right chest.

The left front center band 215, the right front center band 216 and the back center band 231 are made of non-elastic or low-elastic material in regions used for mounting electrodes, and the other regions are made of elastic material so that the electrodes are shaken as small as possible due to a movement of a human body.

The front center band 211 and the back center band 231 may have a width (vertical) of at least 5 cm to 10 cm and a breadth (horizontal) of ¼ of a minimum chest size to ¾ of a maximum chest size and be located at a bust line. In particular, the front center band 211 is installed to cover a point located at a left side by 3 to 5 cm from a cross point of the bust line and the front center.

The front upper central dart 227 is formed to be fit (closely adhered) to a chest surface according to a three-dimensional structure of the cleavage between breasts. In particular, since a top clothing is spaced more at the cleavage portion in comparison to other portions, the chest center elastic member 219 made of an elastic material is provided, and the front upper central dart 227 passes through the center portion of the chest center elastic member 219 so as to be fit to the body (the chest) and ensure more convenient motion.

The back center band 231 has a band shape, and one end of the back center band 231 is mounted to the left elastic member 221 at the rear sheet, and the other end is mounted to the right elastic member 221, across a back center portion.

The back lower central dart 228 is provided to be fit (closely adhered) to a waste surface according to a three-dimensional structure of a spinal curvature of the waist portion in consideration of a concave portion along the spine between the back lower portion and the waste.

Generally, a dart is formed by folding a planar fabric as in a clothing pattern to give a three-dimensional feeling, and the front upper central dart 227 and the back lower central dart 228 may have different locations and sizes according to a portion which demands close adhesion between the clothing and the surface of the human body. Thus, the front upper central dart 227 and the back lower central dart 228 are fabricated suitable for various curves such as cleavage or spine.

Meanwhile, at least one of the front central band 221 and the back central band 231 may be formed at an inner side surface of the clothing, namely at a surface which comes into contact with the skin. Therefore, the front central band 221 and the back central band 231 do not outstand, and electrodes may be disposed at the front central band 221 or the back central band 231 to make direct contact with the skin.

Figure 2B:
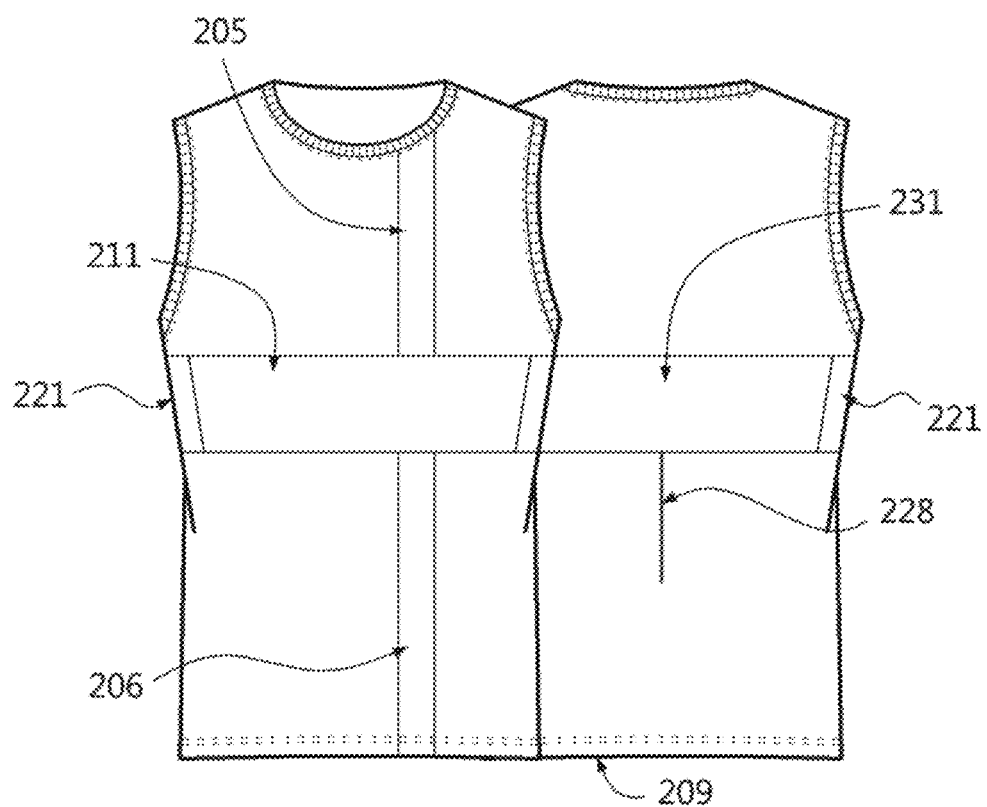
FIG. 2b shows a structure of clothing with a minimized motion artifact, to which a textile electrode kit is mounted according to a second embodiment of the present disclosure.

FIG. 2b shows a structure of clothing with a minimized motion artifact, to which a textile electrode kit is mounted according to a second embodiment of the present disclosure.

In FIG. 2b, the back center band 231, the back lower central dart 228 and the elastic member 221 are substantially identical to those of FIG. 2a.

In FIG. 2b, the front center band 211 and the back center band 231 are connected through the right and left elastic members 221 and includes a first vertical support unit 205 vertically extending from the neckline to an upper portion of the front center band 211 and a second vertical support unit 206 vertically extending from a lower portion of the front center band 211 to the front lower end 209.

Here, the front center band 211 is made of non-elastic material, and one end of the front center band 211 is mounted to one end of the left elastic member 221, and the other end is mounted to one end of the right elastic member 221.

The back center band 231 is made of non-elastic material, and one end of the back center band 231 is connected to the other end of the left elastic member 221, and the other end is mounted to the other end of the right elastic member 221, across the back center portion.

The front center band 211 and the back center band 231 are used for mounting electrodes and are configured to be shaken as small as possible due to a movement of a human body.

The first vertical support unit 205 is made of non-elastic material and supports the front center band 211 to reduce a movement of the front center band 211 due to a movement of a human body together with the second vertical support unit 206. The first vertical support unit 205 is vertically mounted from an intermediate portion between a neckline center of the front sheet and a point where the neckline meets a shoulder line to an upper portion of the front center band 211.

The second vertical support unit 206 is made of non-elastic material and supports the front center band 211 to reduce a movement of the front center band 211 due to a movement of a human body together with the first vertical support unit 205. The second vertical support unit 206 is vertically mounted from a corresponding portion of the first vertical support unit 205 (an intermediate portion between a lower center of the front center band 211 and one end or the other end of the front center band 211) to the front lower end 209, at a lower portion of the front center band 211.

The first vertical support unit 205 and the second vertical support unit 206 are made of non-elastic material or low-elastic material and have a width (vertical) from the front neckline to a horizontal line. The width varies depending on a human body. The breadth (horizontal) is 2 cm to 10 cm and varies depending on a size of an attached electrode. The first vertical support unit 205 and the second vertical support unit 206 are located to form a straight line with a center of an electrode mounted to the front center band 211.

The front center band 211, the back center band 231, the first vertical support unit 205 and the second vertical support unit 206 are made of non-elastic material, and other portions are made of elastic material.

On occasions, a third vertical support unit (not shown) may be further provided at the rear sheet to correspond to the first vertical support unit 205 of the front sheet, and a fourth vertical support (not shown) may be further provided at the rear sheet to correspond to the second vertical support unit 206 of the front sheet.

Figure 2C:
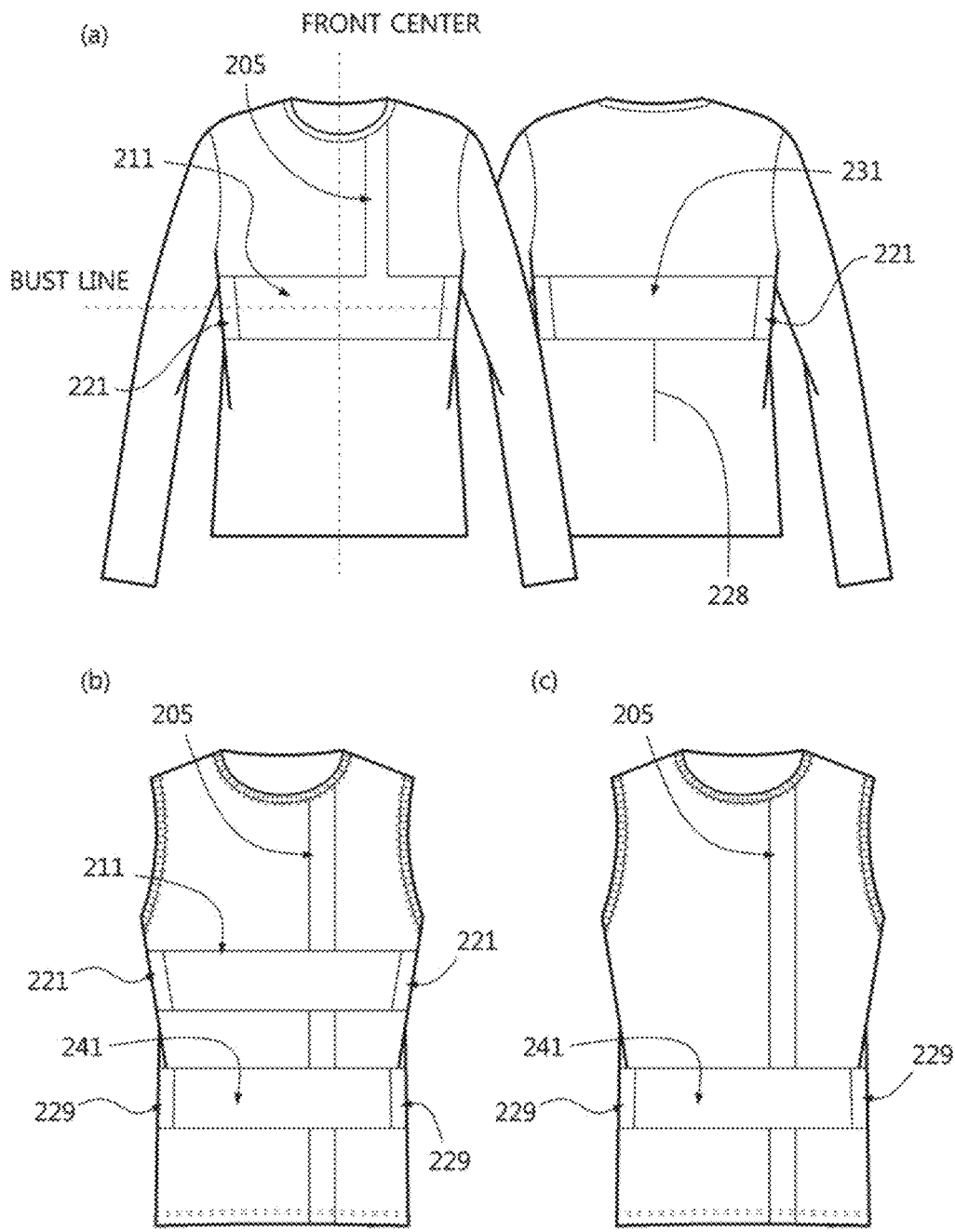
FIG. 2c show structures of clothing with a minimized motion artifact, to which a textile electrode kit is mounted according to another embodiment of the present disclosure.

FIG. 2c show structures of clothing with a minimized motion artifact, to which a textile electrode kit is mounted according to another embodiment of the present disclosure.

Portion (a) of FIG. 2c is substantially identical to FIG. 2b from which the second vertical support unit 206 is excluded, and thus is not described in detail here.

Portion (b) of FIG. 2c includes all components of FIG. 2b and further includes a front abdominal band 241 and a waste sideline elastic members 229. On occasions, a back abdominal band (not shown) may also be further provided.

Here, the waste sideline elastic member 229 is made of elastic material (for example, an elastic band) and mounted to side seams of the right and left waist portion to connect the front abdominal band 241 and the back center band (not shown) or connect the front abdominal band 241 to the rear sheet so as to ensure easily motion even though the front abdominal band 241 made of non-elastic material is provided.

The front abdominal band 241 is made of non-elastic material and disposed at the front sheet of the clothing with a band shape. One end of the front abdominal band 241 is mounted to one end of the left waste sideline elastic member 229, and the other end is mounted to one end of the right waste sideline elastic member 229, across the abdominal area.

The back abdominal band (not shown) is made of non-elastic material and disposed at the rear sheet of the clothing with a band shape. One end of the back abdominal band is mounted to the other end of the left waste sideline elastic member 229, and the other end is mounted to the other end of the right waste sideline elastic member 229, across the back waist portion.

Portion (c) of FIG. 2c is substantially identical to Portion (b) of FIG. 2c from which the front center band 211, the back center band 231 and the under-armpit elastic member 221 are excluded, and all components of Portion (c) of FIG. 2c are identical to those of Portion (b) of FIG. 2c and thus not described in detail here.

In the present disclosure, as shown in FIGS. 2a to 2c, contact-type electrodes or non-contact electrodes may be mounted to the front center band 211, the back center band 231, the front abdominal band 241 and the back abdominal band (not shown) to detect a bio signal. If a contact-type electrode is mounted, the contact-type electrode may be mounted to a portion of the front center band 211, the back center band 231, the front abdominal band 241 and the back abdominal band (not shown), which comes into contact with the skin. If a non-contact electrode is mounted, the non-contact electrode may be mounted to an outer surface of the front center band 211, the back center band 231, the front abdominal band 241 and the back abdominal band (not shown) (namely, a surface opposite to the surface in contact with the human body).

In addition, in FIGS. 2a to 2c, a pocket or tunnel may be provided at the front center band 211, the back center band 231, the front abdominal band 241 and the back abdominal band (not shown), and an electrode may be mounted in the pocket or the tunnel to detect a bio signal.

In FIGS. 2a to 2c, the front center band 211, the back center band 231, the front abdominal band 241 and the back abdominal band (not shown) are depicted as a structure for mounting an electrode, but the present disclosure is not limited thereto, and the present disclosure may have various structures for mounting an electrode.

Figure 2D:
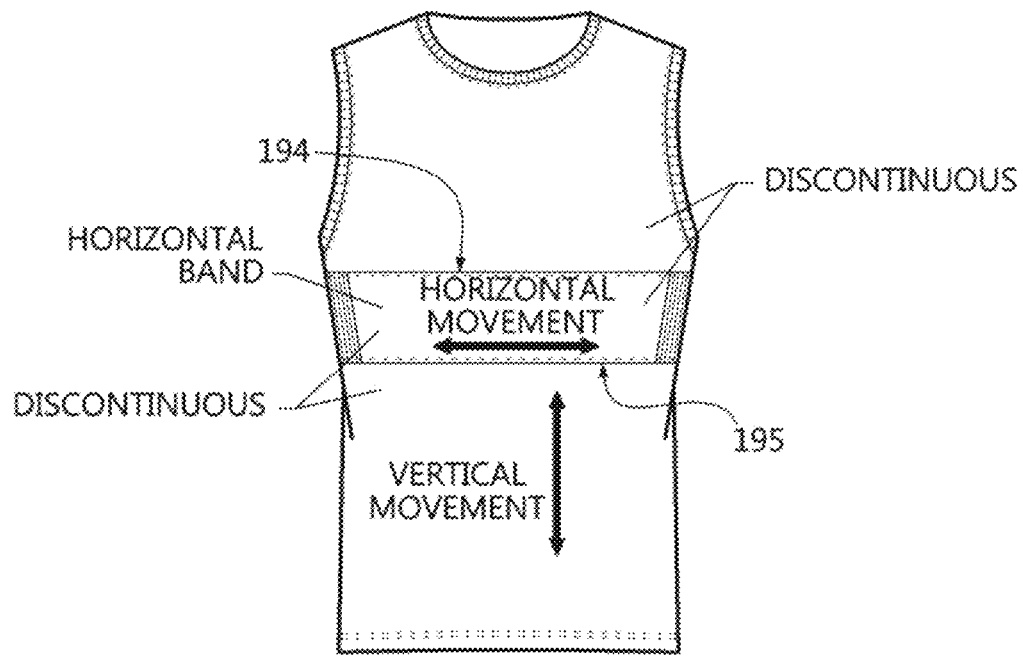
FIG. 2d is a diagram for illustrating a decrease of a motion artifact according to a vertical movement at a horizontal band in the present disclosure.

FIG. 2d is a diagram for illustrating a decrease of a motion artifact according to a vertical movement (upper and lower movement) at a horizontal band in the present disclosure.

If a horizontal band located horizontally at the clothing and made of non-elastic material like the front center band 211, the back center band 231, the front abdominal band 241 and the back abdominal band (not shown) is mounted, since the horizontal band is continuous in a horizontal direction, a horizontal movement of a human body (a horizontal vector) is transferred as it is. In other words, a motion artifact according to the horizontal movement of a human body (namely, right and left movement) (a horizontal vector) is transferred as it is.

However, the lop surface 194 and the bottom surface 195 of the horizontal band are connected to the elastic material, respectively. Even though the top surface 194 is connected to the upper portion of the top surface 194, made of elastic material, the connection portion is a discontinuous portion where the material of the top surface 194 and the material of the upper portion of the top surface 194 are not continuous. Similarly, the connection portion connecting the bottom surface 195 to the lower portion of the bottom surface 195, made of elastic material, is a discontinuous portion where the material of the bottom surface 195 and the material of the lower portion of the bottom surface 195 are not continuous any more.

A vertical movement of a human body (a vertical vector) is substantially not transferred when meeting the discontinuous portion. Therefore, a motion artifact according to the vertical movement of a human body (namely, upper and lower movement) (a vertical vector) is reduced.

Figure 2E:
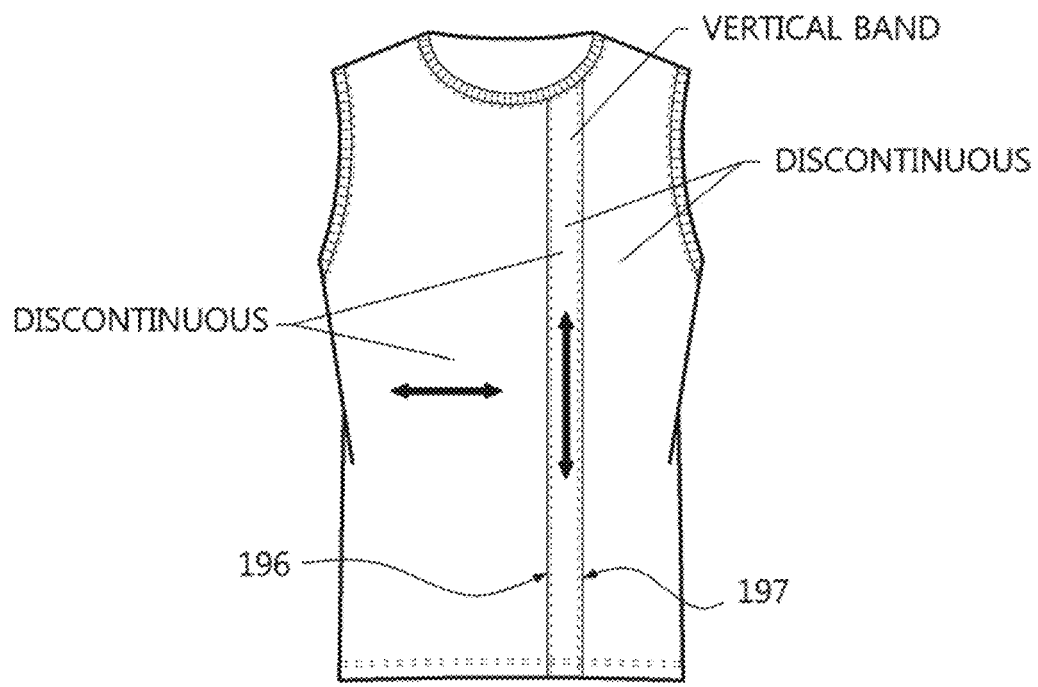
FIG. 2e is a diagram for illustrating a decrease of a motion artifact according to a horizontal movement at a vertical band in the present disclosure.

FIG. 2e is a diagram for illustrating a decrease of a motion artifact according to a horizontal movement (right and left movement) at a vertical band in the present disclosure.

If a vertical band located vertically at the clothing and made of non-elastic material like the first vertical support unit 205 and the second vertical support unit 206 is mounted, since the vertical band is continuous in a vertical direction, a vertical movement of a human body (vertical vector) is transferred as it is. In other words, a motion artifact according to the vertical movement of a human body (namely, upper and lower movement) (a vertical vector) is transferred as it is.

However, the left side surface 196 and the right side surface 197 of the vertical band are connected to the elastic material, respectively. Even though the left side surface 196 is connected to the left side portion of the left side surface 196, made of elastic material, the connection portion is a discontinuous portion where the material of the left side surface 196 and the material of the left side portion of the left side surface 196 are not continuous. Similarly, the connection portion connecting the right side surface 197 to the right side portion of the right side surface 197, made of elastic material, is a discontinuous portion where the material of the right side surface 197 and the material of the right side surface of the right side surface 197 are not continuous any more.

A horizontal movement of a human body (a horizontal vector) is substantially not transferred when meeting the discontinuous portion. Therefore, a motion artifact according to the horizontal movement of a human body (namely, right and left movement) (a horizontal vector) is reduced.

Figure 2F:
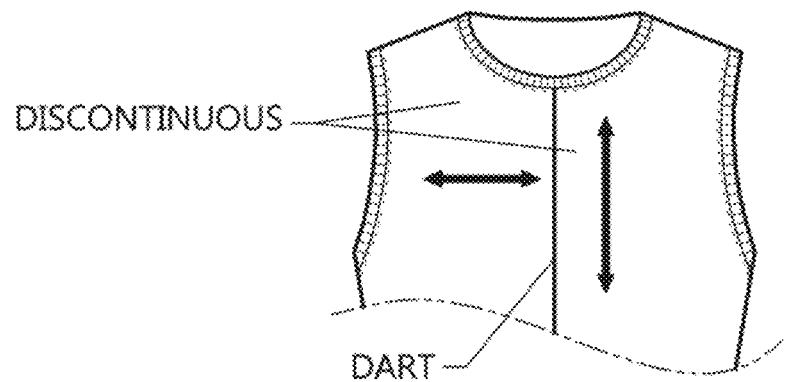
FIG. 2f is a diagram for illustrating a decrease of a motion artifact according to a horizontal movement at a dart vertically located in the present disclosure.

FIG. 2f is a diagram for illustrating a decrease of a motion artifact according to a horizontal movement (right and left movement) at a dart vertically located in the present disclosure.

If the clothing has a dart located in a length direction (a longitudinal direction), both sides of the dart are discontinuous. In other words, since the dart is located vertically, a horizontal movement of a human body is reduced when colliding with the dart. However, a vertical movement of a human body is transferred as it is since there is no obstacle. Therefore, if a dart located in a vertical direction is provided, a motion artifact according to the horizontal movement of a human body (namely, right and left movement) (a horizontal vector) is reduced.

Figure 2G:
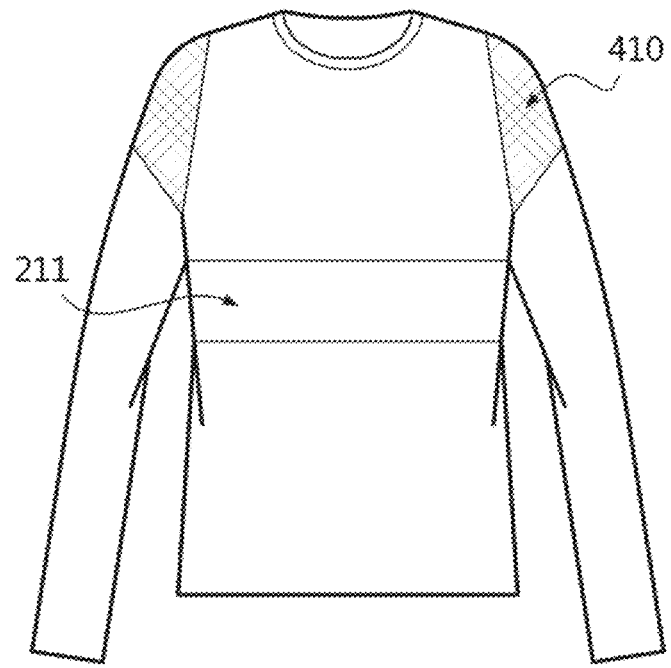
FIG. 2g is a diagram for illustrating a decrease of a motion artifact according to a movement of the arm at a sleeve portion in the present disclosure.

FIG. 2g is a diagram for illustrating a decrease of a motion artifact according to a movement of the arm at a sleeve portion in the present disclosure.

A sleeve portion 410 of the clothing may be formed with a mesh structure having a net pattern, a slit structure having a narrow and long groove, a cut-out structure formed by greatly cutting out a partial portion, a folding structure having a pleat or a pleat structure. If a wearer of the clothing moves the arm, the body sheet of the clothing moves according to the movement of the arm. At this time, if the sleeve portion 410 has a mesh structure, a slit structure or a cut-out structure so that a hole is formed through the sleeve portion 410 which connects the shoulder and the arm of the clothing, even though the arm is moved, only the sleeve portion 410 is shrunken or expand so that the body sheet of the clothing does not move, thereby reducing a motion artifact according to the movement of the arm.

In the same principle, if the sleeve portion 410 has a folding structure or a pleat structure so that a pleat (not shown) is formed at the sleeve portion 410, as the pleat is folded or unfolded according to the movement of the arm, a motion artifact according to the movement of the arm is reduced.

Figure 2H:
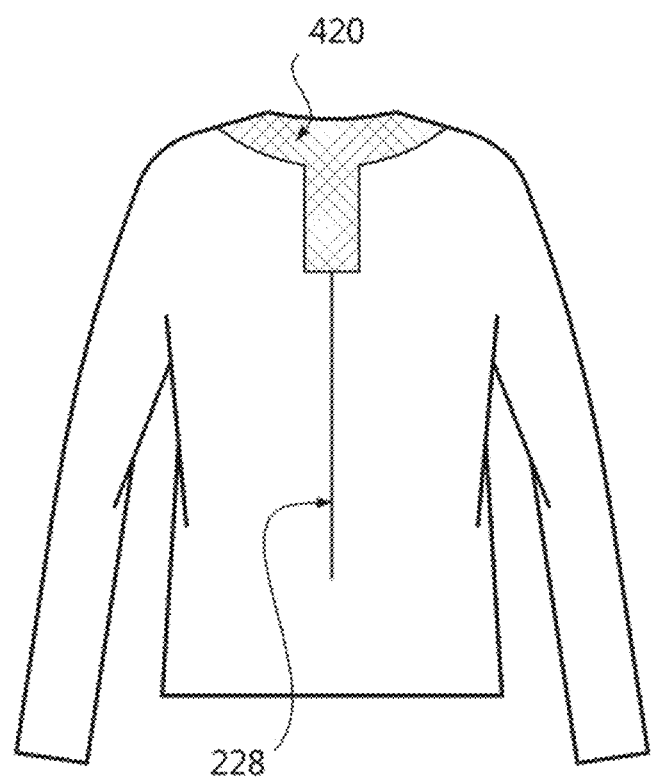
FIG. 2h is a diagram for illustrating a decrease of a motion artifact according to a movement of the cervical spine at a neck girth in the present disclosure.

FIG. 2h is a diagram for illustrating a decrease of a motion artifact according to a movement of the cervical spine at a neck girth in the present disclosure.

A neck girth 420 of the clothing may have a mesh pattern, or a pleat may be formed at the neck girth 420. If a wearer of the clothing moves the neck, the body sheet of the clothing moves according to a movement of the cervical spine. At this time, as described above with reference to FIG. 2h, the neckline 420 has a mesh pattern or a pleat (not shown), thereby reducing a motion artifact according to the movement of the cervical spine.

Figure 3A:
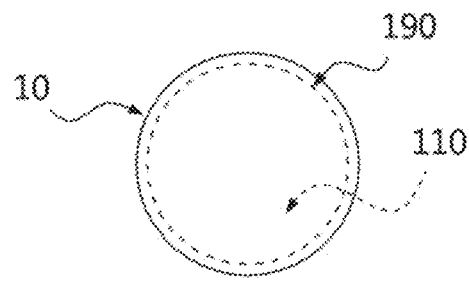
FIG. 3a shows an example of a textile electrode kit according to an embodiment of the present disclosure.
Figure 3B:
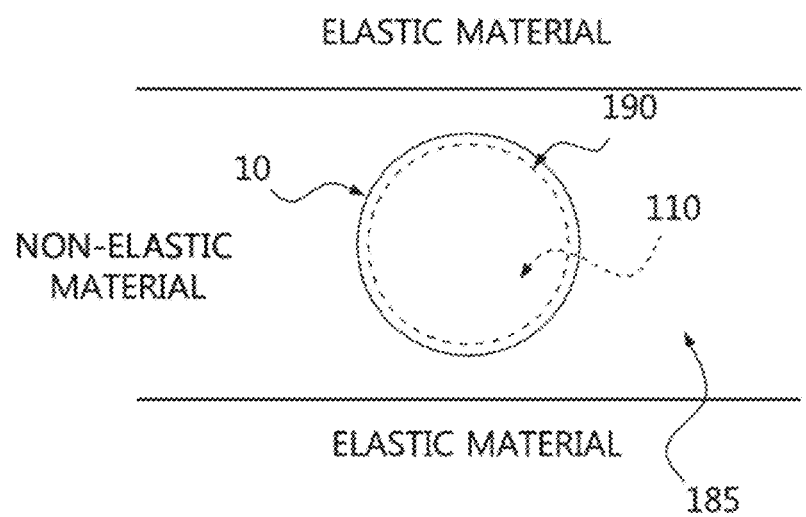
FIG. 3b is a diagram for illustrating an example of clothing to which the textile electrode kit of FIG. 3a is applied.

FIG. 3a shows an example of a textile electrode kit according to an embodiment of the present disclosure, and FIG. 3b is a diagram for illustrating an example of clothing to which the textile electrode kit of FIG. 3a is applied.

The textile electrode kit 10 may be composed of only the electrode 110, composed of the electrode 110 and the three-dimensional structure 140, or composed of the electrode 110, the three-dimensional structure 140 and the signal detection module 130.

If the textile electrode kit 10 is composed of only the electrode 110, the electrode 110 is attached to the clothing electrode mounting portion 185 or coupled thereto by means of sewing 190. If the electrode 110 is a contact-type electrode, the electrode 110 is mounted to an inner side of the clothing electrode mounting portion 185, which is a portion coming into contact with the skin (by attachment or the sewing 190). If the electrode 110 is a non-contact electrode, the electrode 110 may be mounted to an inner or outer side of the clothing electrode mounting portion 185.

Here, the clothing electrode mounting portion 185 is a portion formed at the clothing with non-elastic material for the mounting of an electrode and may be the front center band 211, the back center band 231, the front abdominal band 241, the back abdominal band (not shown) or the like, or a pocket or tunnel formed thereat.

In FIGS. 3a and 3b, even though the textile electrode kit is depicted as having a circular shape for convenience, the present disclosure is not limited thereto, and the textile electrode kit may have various shapes.

If the electrode 110 is a non-contact electrode, the non-contact electrode is formed by mounting a spiral coil 115 on a coil-mounted textile sheet 175. The coil-mounted textile sheet 175 may employ the clothing electrode mounting portion 185, or the textile electrode kit 10 having a non-contact electrode may be mounted to the clothing electrode mounting portion 185. At this time, the electrode 110 receives an oscillation signal from an oscillation circuit and outputs a bio signal.

Figure 4A:
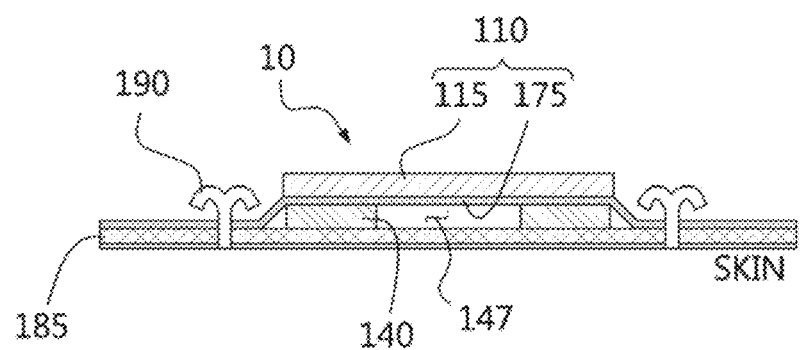
FIG. 4a is a diagram for illustrating a textile electrode kit having a three-dimensional structure below a non-contact electrode according to an embodiment of the present disclosure.
Figure 4B:
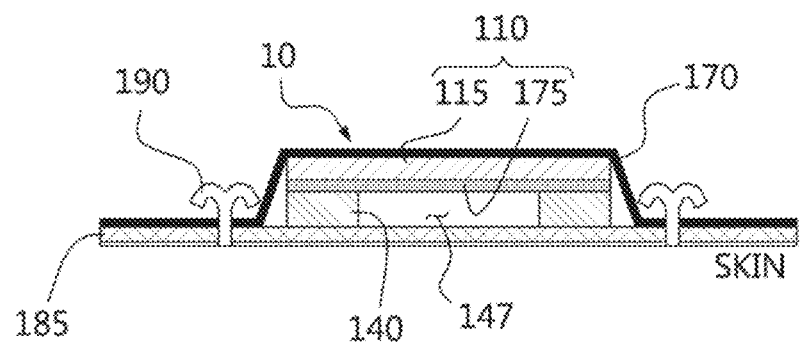
FIG. 4b is a diagram for illustrating a textile electrode kit having a three-dimensional structure below a non-contact electrode according to another embodiment of the present disclosure.

FIG. 4a is a diagram for illustrating a textile electrode kit having a three-dimensional structure below a non-contact electrode according to an embodiment of the present disclosure, and FIG. 4b is a diagram for illustrating a textile electrode kit having a three-dimensional structure below a non-contact electrode according to another embodiment of the present disclosure.

FIGS. 4a and 4b depict a three-dimensional structure 140 having a non-contact electrode formed by mounting the spiral coil 115 on the coil-mounted textile sheet 175, which is provided below the electrode 110, and the clothing electrode mounting portion 185 (or, the lower fixed member) is located below the three-dimensional structure 140.

In FIG. 4a, a rim of the coil-mounted textile sheet 175 is coupled to the clothing electrode mounting portion 185 (or, the lower fixed member). In other words, the rim of the coil-mounted textile sheet 175 is sewed or attached to the clothing electrode mounting portion 185 (or, the lower fixed member).

In FIG. 4b, an upper cover member 170 is further provided, and the rim of the upper cover member 170 is coupled to the clothing electrode mounting portion 185 (or, the lower fixed member). In other words, the rim of the upper cover ember 170 is sewed or attached to the clothing electrode mounting portion 185 (or, the lower fixed member).

The three-dimensional structure 140 has an electrode stabilizing foam (a buffering member) and is stably mounted to a human body while being less influenced by a movement of the human body even though the human body has bent portions, in order to reduce a motion artifact at the electrode 110 and buffer an external pressure. The three-dimensional structure 140 may employ any three-dimensional structure such as memory foam, sponge, Styrofoam, fabric or the like.

A single three-dimensional structure 140 is a single continuous material, which receives a movement of a human body at a bottom surface of the three-dimensional structure 140 and a portion in contact with the skin and transfers the movement to the electrode 110 through the upper surface of the single three-dimensional structure 140. Therefore, if the size of the cushion member 140 is reduced and the cushion members 140 are spaced to form a discontinuous space 147 between the cushion members 140, a motion artifact is not transferred in the discontinuous space 147, and as a result, the motion artifact transferred to the electrode 110 is reduced as much as the reduced area of the cushion member 140 and the increased area of the discontinuous space 147.

The lower fixed member (not shown) is located below the three-dimensional structure 140 to cover the lower portion of the textile electrode kit 10 and may be made of various materials such as fabric, rubber, vinyl, film, plastic or the like. At this time, the fabric may include a clothing fabric. If the lower fixed member is provided, the electrode 110 is not directly mounted to the clothing electrode mounting portion 185, and the textile electrode kit 10 may be freely used individually.

The upper cover member 170 is located above the spiral coil 115 to surround and cover the electrode 110 and may be made of various materials such as fabric, rubber, vinyl, film, plastic or the like.

Figure 5A:
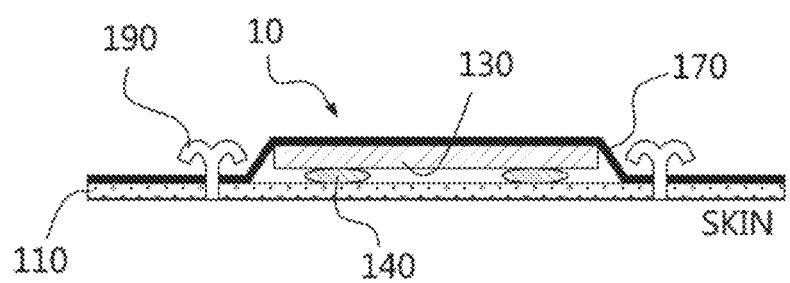
FIG. 5a is a diagram for illustrating a textile electrode kit having a three-dimensional structure above a non-contact electrode according to an embodiment of the present disclosure.
Figure 5B:
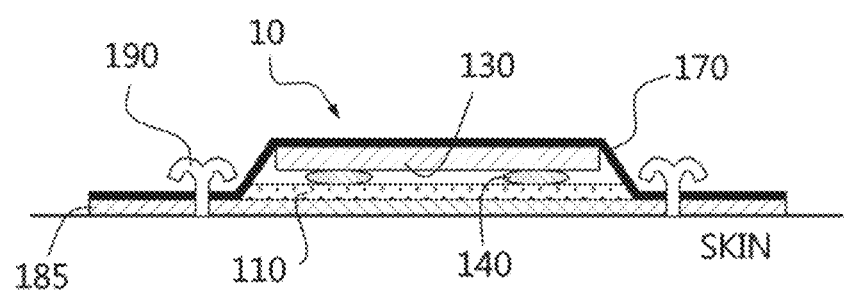
FIG. 5b is a diagram for illustrating a textile electrode kit having a three-dimensional structure above a non-contact electrode according to another embodiment of the present disclosure.

FIG. 5a is a diagram for illustrating a textile electrode kit having a three-dimensional structure above a non-contact electrode according to an embodiment of the present disclosure, and FIG. 5b is a diagram for illustrating a textile electrode kit having a three-dimensional structure above a non-contact electrode according to another embodiment of the present disclosure.

In FIGS. 5a and 5b, an electrode 110 is provided, a three-dimensional structure 140 is located thereon, a signal detection module 130 is located thereon, and an upper cover member 170 is provided thereon. Here, the electrode 110 is a non-contact electrode, which is formed by mounting the spiral coil 115 on the coil-mounted textile sheet 175.

In FIG. 5a, the coil-mounted textile sheet 175 and the upper cover member 170 are coupled. In other words, a rim of the coil-mounted textile sheet 175 is sewed or attached to the upper cover member 170. In this case, the electrode 110 is not directly mounted to the clothing electrode mounting portion 185, and the textile electrode kit 10 may be freely used individually.

In FIG. 5b, the upper cover member 170 is coupled to the clothing electrode mounting portion 185 (or, the lower fixed member). Here, a rim of the upper cover member 170 is sewed or attached to the clothing electrode mounting portion 185 (or, the lower fixed member), which means that the upper cover member 170 is directly mounted to the clothing.

The signal detection module 130 drives the electrode 110 to detect a bio signal and is mounted in a housing. In case of a non-contact electrode, the signal detection module 130 includes an electrode driving unit 139 and a signal pre-processing unit 133.

The electrode driving unit 139 has an oscillation circuit composed of L and C and transmits an oscillation signal to a coil which is a non-contact electrode.

The signal pre-processing unit 133 demodulates the oscillation signal received from the coil which is a non-contact electrode to detect a bio amplifies the bio signal, and removes artifact.

If the electrode 110 is a non-contact electrode, namely having a coil-type magnetic induction sensor which forms a spiral coil on a textile sheet as shown in FIG. 5a, the textile electrode kit 10 may be formed by sewing an outer portion (a circumferential portion) of the textile sheet of the electrode 110 and an outer portion of the upper cover member 170 together in a state of including the three-dimensional structure 140 and the signal detection module 130 therein. The prepared textile electrode kit 10 may be installed at an electrode-mounting tunnel or pocket located at a predetermined position of the clothing.

In addition, as shown in FIG. 5b, the clothing electrode mounting portion 185 (or, the lower fixed member) may be sewed to the outer portion of the upper cover member 170 to fix and mount the textile electrode kit 10 at a predetermined position of the clothing.

In the present disclosure, a wire may be used to connect the electrode 110 to the signal detection module 130 so as to transmit a signal. On occasions, a snap button may also be used.

Figure 6:
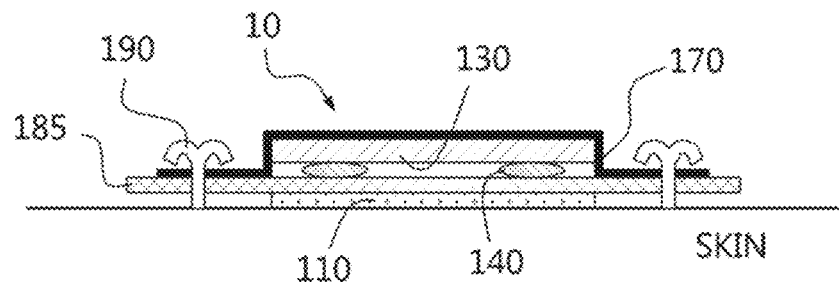
FIG. 6 is a diagram for illustrating a textile electrode kit when the electrode of FIG. 3a is a contact-type electrode sewed together with the clothing.

FIG. 6 is a diagram for illustrating a textile electrode kit having a three-dimensional structure above a contact-type electrode according to an embodiment of the present disclosure.

In FIG. 6, the electrode 110, which is a contact-type electrode, is mounted to a portion of the clothing electrode mounting portion 185 which comes into contact with the skin, a three-dimensional structure 140 is located on the clothing electrode mounting portion 185, a signal detection module 130 is located thereon, and an upper cover member 170 is provided thereon. The upper cover member 170 and the clothing electrode mounting portion 185 are sewed or attached.

The signal detection module 130 drives the electrode 110 to detect a bio signal and is mounted in a housing. In case of a contact-type electrode, the signal detection module 130 includes a signal pre-processing unit 133 for amplifying a signal and removing artifact.

In the present disclosure, the electrode 110 is used for detecting a bio signal and may be either a contact-type electrode for detecting a bio signal in direct contact with the skin or a non-contact electrode for detecting a bio signal by using a coil-type magnetic induction sensor without direct contact with the skin.

If the electrode 110 is mounted to a portion of the clothing electrode mounting portion 185 which comes into contact with the skin, the electrode 110 may be sewed, adhered or mounted by means of a coupling member such as a snap button, depending on the material of the electrode.

As shown in FIG. 3b, regardless of whether the electrode 110 is a non-contact electrode or a contact-type electrode, a portion of the clothing electrode mounting portion 185 where the textile electrode kit 10 is located is made of an non-elastic material. Other portions of the clothing may be made of elastic material. The non-elastic material may be selected from various materials such as cotton and hemp, and the elastic material may be selected from various materials such as polyester, polyurethane, a mixture of polyester and polyurethane or the like.

Even though the lower fixed member and the upper cover member are illustrated as textile in the present disclosure for convenience, the present disclosure is not limited thereto, and in the present disclosure, the lower fixed member and the upper cover member may be made of various flexible materials such as film and vinyl.

Figure 7A:
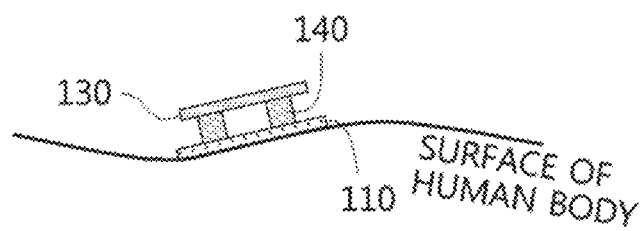
FIG. 7a is a diagram for illustrating a role of a three-dimensional structure, in case of a textile electrode kit having the three-dimensional structure above the electrode, in the present disclosure.
Figure 7B:
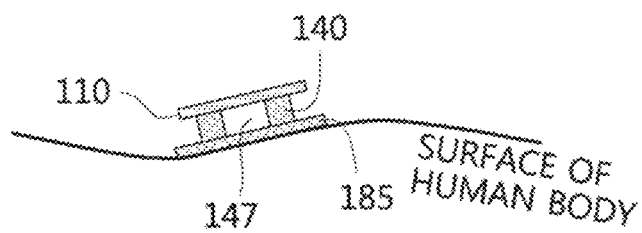
FIG. 7b is a diagram for illustrating a role of a three-dimensional structure, in case of a textile electrode kit having the three-dimensional structure below the electrode, in the present disclosure.

FIG. 7a is a diagram for illustrating a role of a three-dimensional structure, in case of a textile electrode kit having the three-dimensional structure above the electrode, in the present disclosure, and FIG. 7b is a diagram for illustrating a role of a three-dimensional structure, in case of a textile electrode kit having the three-dimensional structure below the electrode, in the present disclosure.

In FIG. 7a, similar to FIGS. 5a, 5b and 6, if the electrode 110 is located at a bent portion of a human body, artifact of a motion artifact or the like increases during a movement of a subject person, and thus a signal may not be normally detected. To solve this problem, in the present disclosure, the three-dimensional structure 140 is interposed between the electrode 110 and the housed signal detection module 130 so that the electrode 110 may be fit to a human body without moving, and thus it is possible to stably detect a signal while reducing a motion artifact during a movement of the subject person.

In FIG. 7b, similar to FIGS. 4a and 4b, if the electrode 110 is located at a bent portion of a human body, artifact of a motion artifact or the like increases even by a little movement of a subject person, and thus a signal may not be normally detected. Therefore, in FIG. 7b, the cushion member 140 is interposed between the electrode 110 and the human body so that the electrode 110, which is a non-contact electrode, may be spaced apart from the human body and less influenced by the movement of the human body. In particular, if the size of the cushion member 140 is reduced and the cushion members 140 are spaced to form a discontinuous space 147 between the cushion members 140, a motion artifact is not transferred in the discontinuous space 147, and as a result, the motion artifact transferred to the electrode 110 is reduced as much as the reduced area of the cushion member 140 and the increased area of the discontinuous space 147. By doing so, it is possible to stably detect a signal while reducing a motion artifact (a motion artifact) during a movement of the subject person.

Figure 8:
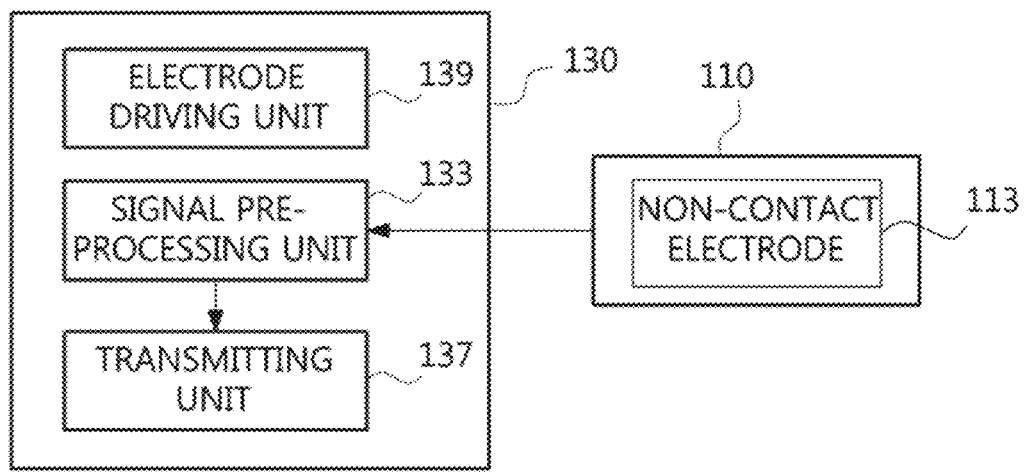
FIG. 8 is a block diagram for illustrating a configuration of a signal detection module having a non-contact electrode.
Figure 9:
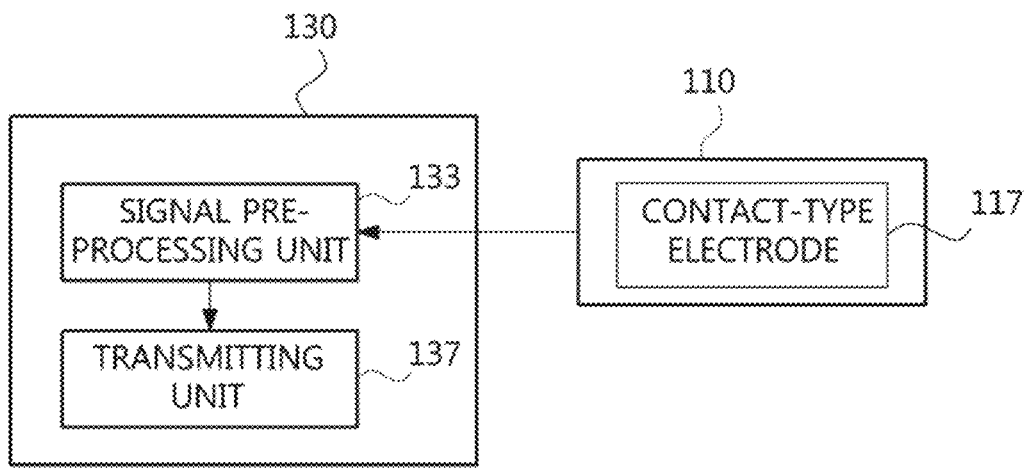
FIG. 9 is a block diagram for illustrating a configuration of the signal detection module having a contact-type electrode.

FIG. 8 is a block diagram for illustrating a configuration of a signal detection module in case of having a non-contact electrode, and FIG. 9 is a block diagram for illustrating a configuration of the signal detection module having a contact-type electrode.

As in FIG. 8, in case of a non-contact electrode (namely, an inductor-type bio signal measurement sensor), the signal detection module 130 includes an electrode driving unit 139, a signal pre-processing unit 133 and a transmitting unit 137.

The electrode driving unit 139 includes an oscillation circuit composed of L and C and transmits an oscillation signal to the non-contact electrode 113. If so, a magnetic field is formed by a minute current flowing on the coil of the non-contact electrode 113. The magnetic field varying according to time induces an eddy current in the detection target (in the human body), and the induced current generates a minute magnetic field in a direction opposite to the magnetic field generated at the coil of the non-contact electrode 113.

The signal pre-processing unit 133 includes a demodulating unit (not shown), an amplifier (not shown) and a filter (not shown), demodulates an oscillation signal received from the non-contact electrode 113 to detect a bio signal, amplifies the bio signal, and removes artifact.

The transmitting unit 137 transmits the bio signal detected by the signal pre-processing unit 133. The transmitting unit 137 may employ wireless transmitting unit or a wireless transmission port for transmitting signals in a wired manner. In case of the wireless transmission port, a snap button or a connector may be employed.

As shown in FIG. 9, the signal detection module 130 which is a contact-type electrode 117 includes a signal pre-processing unit 133 and a transmitting unit 137.

The signal pre-processing unit 133 includes an amplifier (not shown) and a filter (not shown) to amplifiers the bio signal received from the contact-type electrode 117 and remove artifact.

The transmitting unit 137 transmits the bio signal detected by the signal pre-processing unit 133, and the transmitting unit 137 may be a wireless transmitting unit or a wireless transmission port for transmitting signals in a wired manner.

Figure 10:
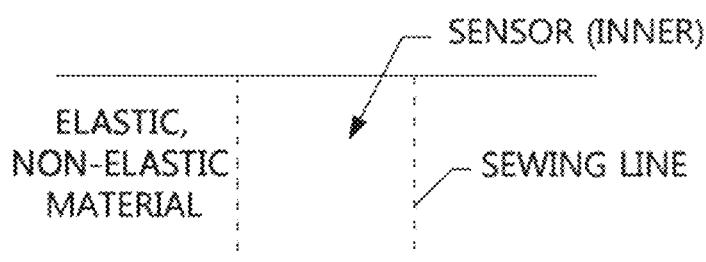
FIG. 10 is a diagram for illustrating an electrode-mounting tunnel for mounting the textile electrode kit to the clothing according to the present disclosure.
Figure 11:
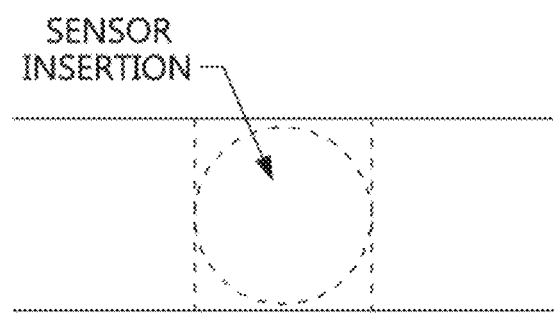
FIG. 11 is a diagram for illustrating a case in which the textile electrode kit is inserted into the electrode-mounting tunnel of FIG. 10.

FIG. 10 is a diagram for illustrating an electrode-mounting tunnel for mounting the textile electrode kit to the clothing according to the present disclosure, and FIG. 11 is a diagram for illustrating a case in which the textile electrode kit is inserted into the electrode-mounting tunnel of FIG. 10.

As shown in FIG. 10, an electrode-mounting tunnel (or, an electrode-mounting pocket) for mounting the textile electrode kit 10 to the clothing is formed by sewing two textile sheets. Here, the lower textile sheet may be made of non-elastic material, and the upper textile sheet may be elastic material. The electrode-mounting tunnel is formed by sewing right and left portions of the electrode-mounting tunnel as shown in FIG. 10, and thus two entrances are formed at the upper and lower portions.

The electrode-mounting pocket is formed by sewing right and left portions of the electrode-mounting tunnel and then further sewing one of upper and lower sides so that an entrance is formed at the other of the upper and lower sides. Here, the term "upper", "lower". "right" and "left" represents a direction indicated by four terminals in the cross shape, without being limited to upper, lower, right and left parts of the clothing.

As shown in FIG. 11, the textile electrode kit 10 is inserted by pressure into the entrance of the electrode-mounting tunnel.

Even though FIGS. 10 and 11 depict a straight tunnel structure, the present disclosure is not limited thereto but may have various tunnel structures such as a cross shape, a straight shape, a T shape, an inversed T shape, an O shape, a rectangular shape, a diamond shape, a triangular shape, a V shape, a "=" shape, a "≡" shape, a "∓" shape, an X shape, a radial shape or the like at the front, rear and side surfaces of the clothing.

Figure 12:
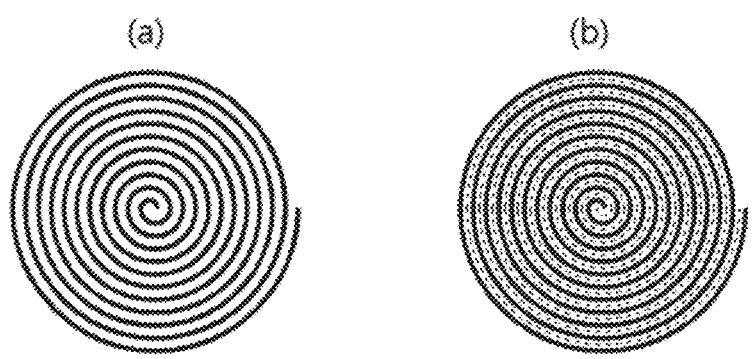
FIG. 12 shows an example of the non-contact electrode employed in the present disclosure.

FIG. 12 shows an example of the non-contact electrode employed in the present disclosure.

Portion a) of FIG. 12 shows an example of a non-contact electrode in which a circular spiral coil is formed on a textile sheet, and as shown in Portion b) of FIG. 12, it is also possible that a spiral coil is formed on a textile sheet and the coil wires are stitched using an insulating thread.

Even though FIG. 12 depicts that the non-contact electrode is circular, the present disclosure is not limited thereto, but the non-contact electrode of the present disclosure may have various shapes such as a rectangular shape, a diamond shape or the like.

In addition, the spiral coil on the textile sheet may be formed by embroidering, weaving or knitting a conductive thread, adhering a textile sheet with a conductive material, or printing a conductive material on a textile sheet.

Figure 13:
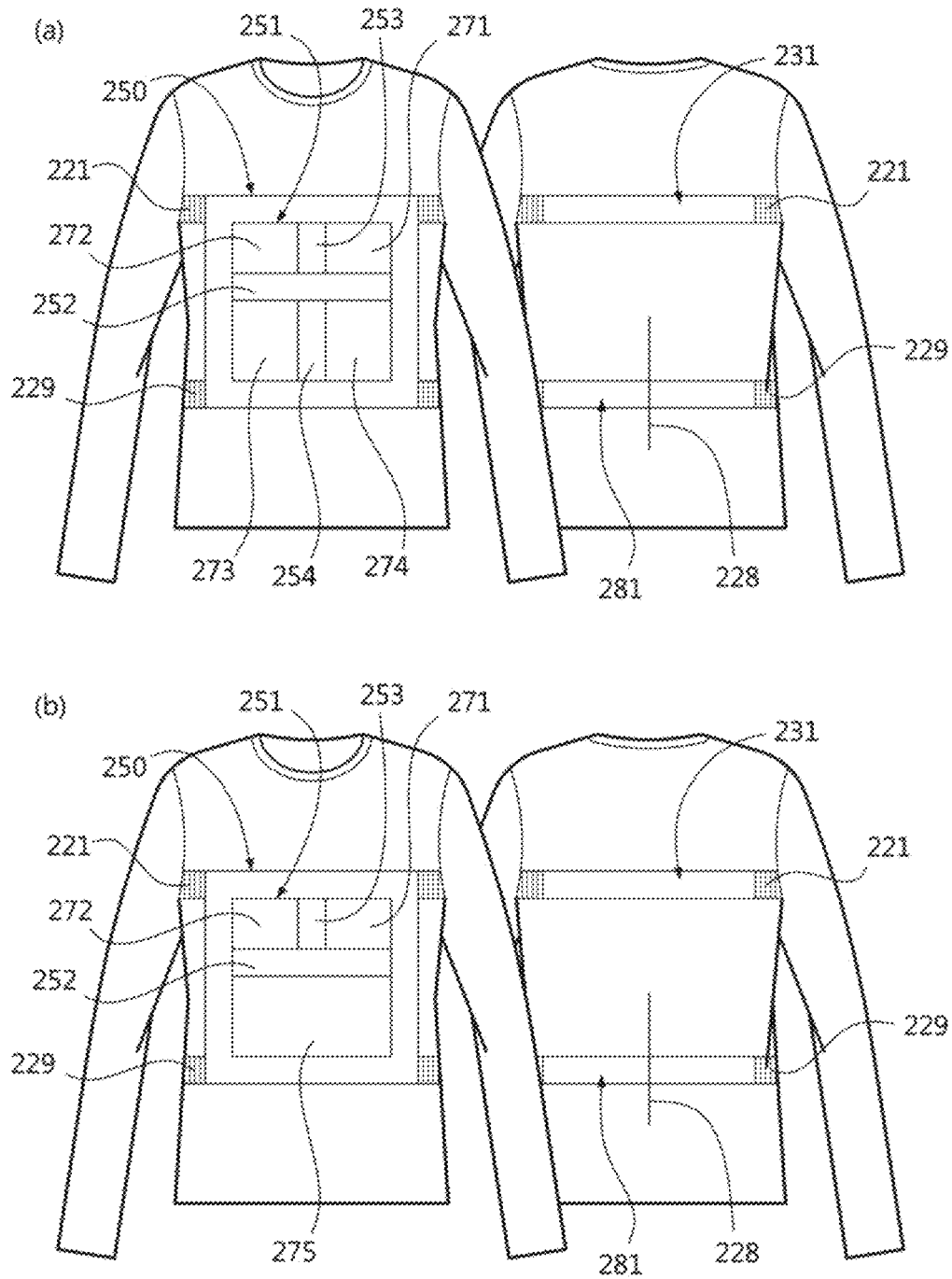
FIG. 13 shows structures of clothing with a minimized motion artifact having a front rectangular non-elastic unit in the present disclosure.

FIG. 13 shows structures of clothing with a minimized motion artifact having a front rectangular non-elastic unit in the present disclosure.

A rectangular non-elastic unit 250 is located at the front sheet, is made of non-elastic material and has a plurality of cut lines. Portions (a) of FIG. 13 has a rectangular non-elastic unit 250 formed by cut lines with a '⊞' shape, and Portion (b) of FIG. 13 has a rectangular non-elastic unit 250, where an in-square lower vertical support unit 254 is excluded from Portion (a) of FIG. 13.

A rectangular cut line 251 is provided in the rectangular non-elastic unit 250 at the front sheet of Portion (a) of FIG. 13, and an in-square horizontal support unit 252 formed by two horizontal cut lines is provided at an intermediate portion in the rectangular cut line 251. An in-square upper vertical support unit 253 extending from an intermediate upper portion of the in-square horizontal support unit 252 to a top surface of the rectangular cut line 251 is provided. In addition, an in-square lower vertical support unit 254 extending from an intermediate lower portion of the in-square horizontal support unit 252 to a center of the lower surface of the rectangular cut line 251 is provided. By means of the in-square horizontal support unit 252, the in-square upper vertical support unit 253 and the in-square lower vertical support unit 254, other areas are divided into quadrants, namely, a quadrant I 271, a quadrant II 272, a quadrant III 273 and a quadrant IV 274, which has a 田 shape.

The right and left elastic members 221, the back center band 231, the waste sideline elastic members 229 and the back lower central dart 228 at the rear sheet of Portion (a) of FIG. 13 are already described above, and are not explained in detail her. The back abdominal band 281 is located on an extension line of the front abdominal band 241 and is located at an abdominal portion of the rear sheet, namely at a waist portion of the rear sheet.

Portion (b) of FIG. 13 shows that the rectangular non-elastic unit 250 includes the rectangular cut line 251, the in-square horizontal support unit 252, the in-square upper vertical support unit 253, the quadrant 271, the quadrant II 272, the right and left elastic members 221, the back center band 231, the waste sideline elastic members 229, the back lower central dart 228 and the back abdominal band 281, which is identical to Portion (a) of FIG. 13 and not described in detail here.

At the front sheet of Portion (b) of FIG. 13, an in-square lower support unit 275 is provided below the in-square horizontal support unit 252 in the rectangular cut line 251.

The electrode may be mounted to any location of the rectangular non-elastic unit 250. In case of detecting an electrocardiogram (ECG) signal or a heart activity signal, the electrode is mounted to the quadrant II 272, the quadrant I 271 or the in-square horizontal support unit 252.

Meanwhile, in the present disclosure, though not shown in the figures, a C-shaped non-elastic unit made of non-elastic material or low-elastic material with a "C" shape and an inversed C-shaped non-elastic unit whose "C" shape is symmetric to the above based on the vertical axis may be provided. At this time, the C-shaped non-elastic unit and the inversed C-shaped non-elastic unit are symmetrically disposed based on the vertical axis so that their curved portions come into contact with each other. In other words, as a whole, the C-shaped non-elastic unit and the inversed C-shaped non-elastic unit are disposed at the front sheet with a shape similar to "X". In addition, a band-type elastic member made of high-elastic or elastic material with a band shape may be disposed at the front sheet. At this time, the C-shaped non-elastic unit and the inversed C-shaped non-elastic unit are disposed across the band-type elastic member. However, the C-shaped non-elastic unit and the inversed C-shaped non-elastic unit may not overlap with the band-type elastic member, and a plurality of band-type elastic members may be placed on a straight line in contact with the C-shaped non-elastic unit and the inversed C-shaped non-elastic unit.

In addition, in the present disclosure, though not shown in the figures, an non-elastic unit made of non-elastic material or low-elastic material with a "⊂" shape and an inversed ⊂-shaped non-elastic unit whose "⊂" shape is symmetric to the above based on the vertical axis may be provided. The ⊂-shaped non-elastic unit and the inversed ⊂-shaped non-elastic unit are symmetrically disposed based on the vertical axis so that vertical portions of the "⊂" shape and the "inversed ⊂" shape come into contact with each other. In addition, a band-type elastic member made of high-elastic or elastic material with a band shape may be disposed at the front sheet. At this time, as described above, the ⊂-shaped non-elastic unit and the inversed ⊂-shaped non-elastic unit are disposed across the band-type elastic member.

In addition, in the present disclosure, though not shown in the figures, an L-shaped non-elastic unit made of non-elastic material or low-elastic material with an "L" shape and an inversed L-shaped non-elastic unit whose "L" shape is symmetric to the above based on the vertical axis may be provided. The L-shaped non-elastic unit and the inversed L-shaped non-elastic unit are symmetrically disposed based on the vertical axis so that vertical portions of the "L" and the "inversed L" come into contact with each other or overlap with each other. At this time, the contact or overlapped portions of the "L" and the "inversed L" may be made of high-elastic or elastic material.

Figure 14A:
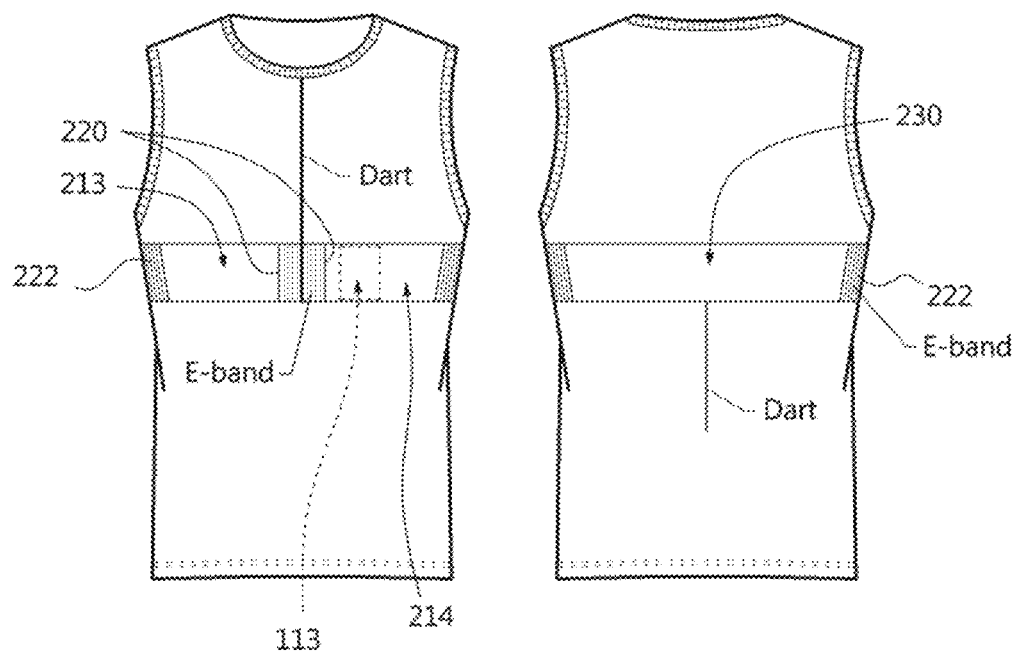
FIG. 14a shows an example of a case in which the clothing to which a textile kit is mounted according to the present disclosure has a chest tunnel.
Figure 14B:
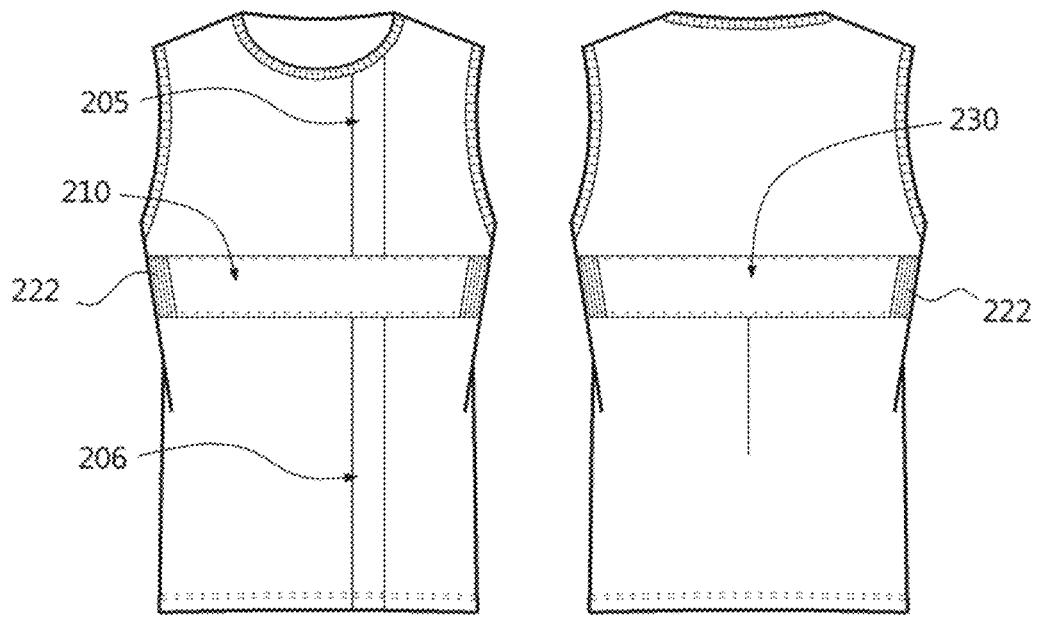
FIG. 14b shows an example of a case in which the clothing to which a textile kit is mounted according to the present disclosure has a vertical support unit and a chest tunnel.
Figure 14C:
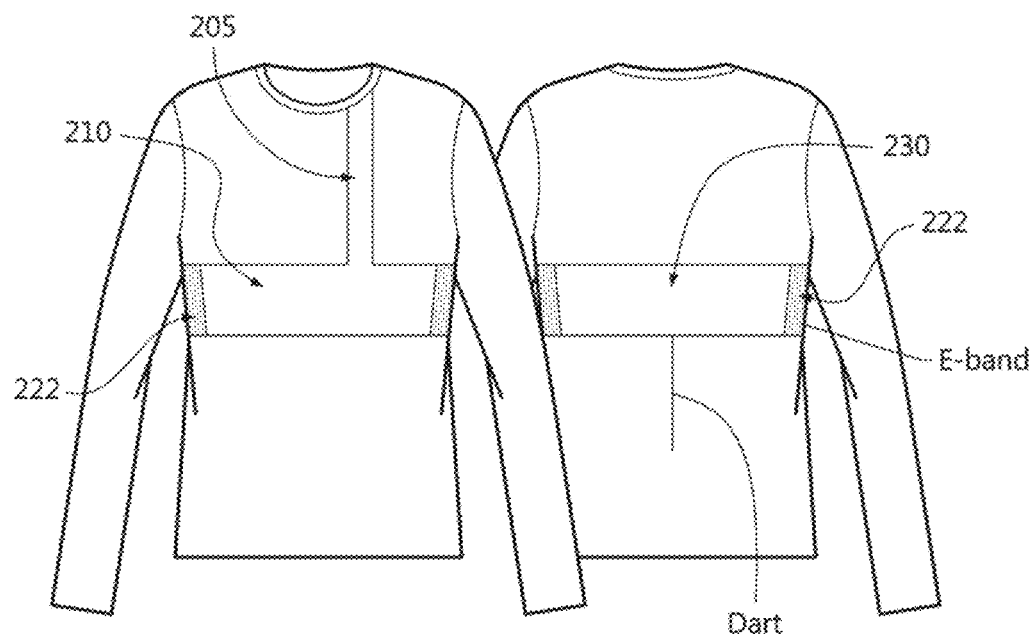
FIG. 14c shows another example of a case in which the clothing to which a textile kit is mounted according to the present disclosure has a vertical support unit and a chest tunnel.

FIG. 14*a* shows an example of a case in which the clothing to which a textile kit is mounted according to the present disclosure has a chest tunnel, FIG. 14*b* shows an example of a case in which the clothing to which a textile kit is mounted according to the present disclosure has a vertical support unit and a chest tunnel, and FIG. 14*c* shows another example of a case in which the clothing to which a textile kit is mounted according to the present disclosure has a vertical support unit and a chest tunnel.

FIG. 14*a* shows an example of the clothing in which tunnels are formed at the front sides of the front center band 211 and the back center band 231 of the clothing of FIG. 2*a*. At the front sheet, a left chest tunnel 213 and a right chest tunnel 214 are provided at right and left sides below the chest (in more detail, above the front center band 211), and at the rear sheet, a back center tunnel 230 may be provided at a location extending from the right and left chest tunnels 213, 214 (in more detail, above the back center band 231). In addition, a central entrance 220 is provided at the center of the front sheet so that the left chest tunnel 213 and the right chest tunnel 214 are inserted therein, and side entrances 222 are provided at the left side surface of the left chest tunnel 213, the right side surface of the right chest tunnel 213 and the left side surface and the right side surface of the back center tunnel 230. By means of the central entrance 220 or the side entrance 222, the textile electrode kit 10 may be properly located at a desired position. An E-band (or, an elastic band) may be mounted to the central entrance 220 and the side entrance 222 so that the textile electrode kit 10 may be easily inserted or separated.

FIG. 14*b* shows an example in which tunnels are formed at the front sides of the front center band 211 and the back center band 231 of the clothing of FIG. 2*b*, and FIG. 14*c* shows an example in which tunnels are formed at the front sides of the front center band 211 and the back center band 231 of the clothing of Portion (a) of FIG. 2*c*.

The clothing of FIGS. 14*b* and 14*c* includes a chest tunnel 210 below the chest (in more detail, above the front center band 211) at the front sheet, and also includes a back center tunnel 230 extending from the chest tunnel 210 at the rear sheet. In addition, side entrances 222 are provided at the left side surface and the right side surface of the chest tunnel 210 at the center of the front sheet, side entrances 222 are also provided at the left side surface and the right side surface back of the center tunnel 230, and the textile electrode kit 10 may be properly located at a desired position by means of the side entrances 222.

The left chest tunnel 213, the right chest tunnel 214 and the chest tunnel 210 of FIGS. 14*a* and 14*b* may be useful for attaching electrodes at both right and left sides of the chest, similar to the electrocardiogram (ECG) electrodes.

Figure 15:
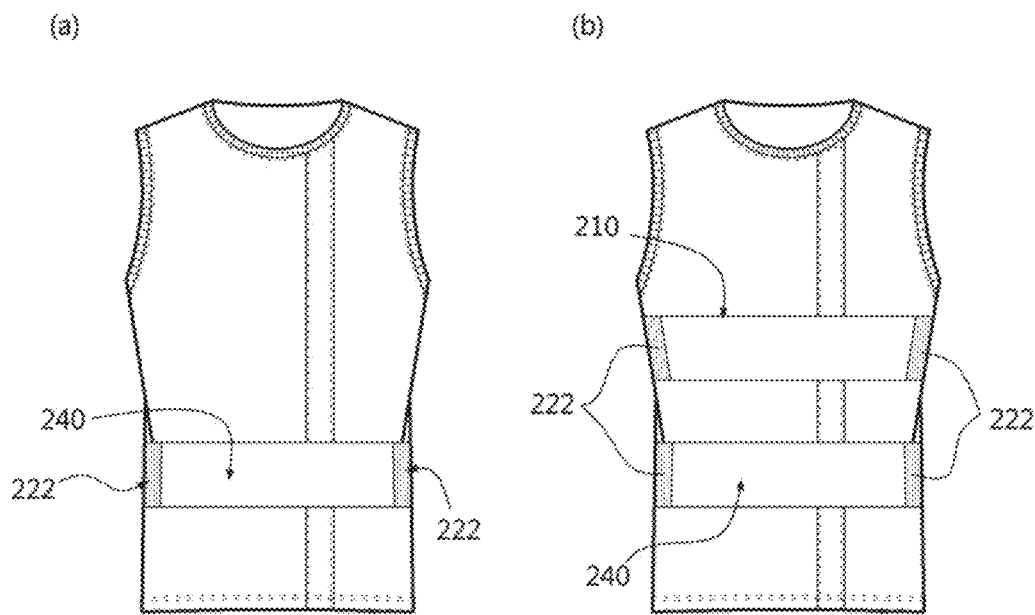
FIG. 15 shows an example of a case in which the clothing to which a textile kit is mounted according to the present disclosure has an abdominal tunnel.

FIG. 15 shows an example of a case in which the clothing to which a textile kit is mounted according to the present disclosure has an abdominal tunnel.

The clothing of Portion (a) of FIG. 15 includes an abdominal tunnel 240 at the front abdominal band 241 depicted in Portion (c) of FIG. 2*c*. Here, a tunnel is formed at an abdominal portion of the front sheet, and side entrances 222 are provided at the left side surface and the right side surface of the abdominal tunnel 240. By doing so, electrocardiogram (ECG) of a fetus may be detected from a mother.

Portion (b) of FIG. 15 shows a case in which the chest tunnel 210 is provided to the front center band 211 depicted in (b) of FIG. 2c and the abdominal tunnel 240 is provided to the front abdominal band 241. By doing so, electrocardiogram (ECG) of a fetus and electrocardiogram (ECG) of a mother may be detected simultaneously.

Figure 16:
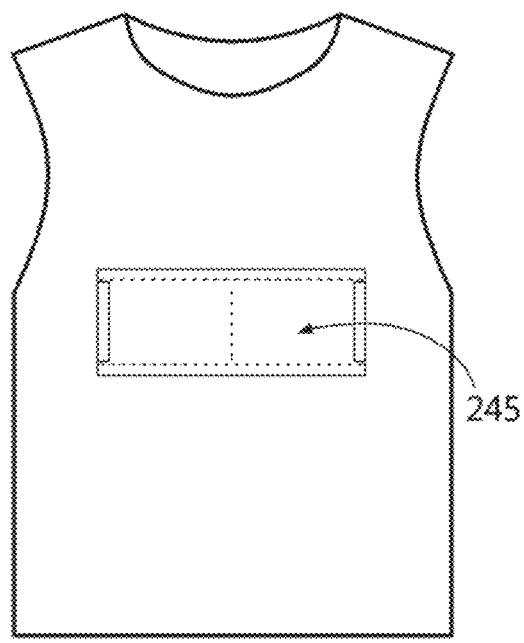
FIG. 16 shows an example of a case in which the clothing to which a textile kit is mounted according to the present disclosure has two chest electrode-mounting pockets.

FIG. 16 shows an example of a case in which the clothing to which a textile kit is mounted according to the present disclosure has two chest electrode-mounting pockets. Here, an electrode-mounting pocket 245 is formed on the chest portion at a position where an electrode is to be mounted, and a textile kit is mounted to the pocket. Even though FIG. 16 depicts that pocket entrances are formed at right and left portions, a pocket entrance may also be formed at a center portion. FIG. 16 may be used when detecting electrocardiogram (ECG).

Figure 17:
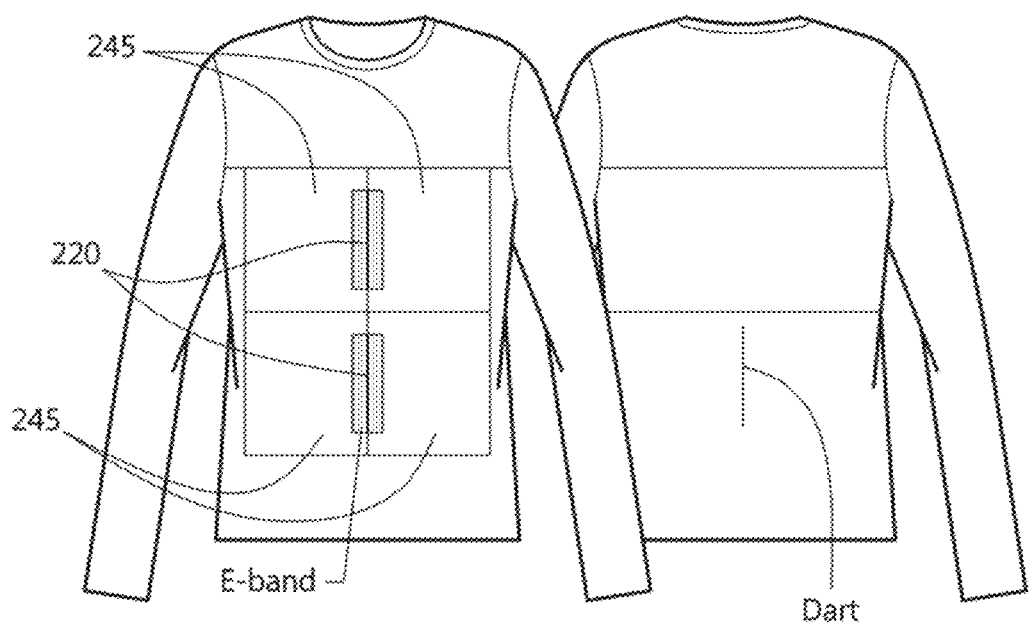
FIG. 17 shows an example of a case in which the clothing to which a textile kit is mounted according to the present disclosure has four electrode-mounting pockets at the front sheet.

FIG. 17 shows an example of a case in which the clothing to which a textile kit is mounted according to the present disclosure has four electrode-mounting pockets at the front sheet. Here, a pocket is formed at the clothing of Portion (a) of FIG. 13, and two electrode-mounting pockets 245 are provided at the chest portion and two electrode-mounting pockets 245 are provided at the abdominal portion. Even though FIG. 17 depicts that the central entrance 220 serving as a pocket entrance is formed at the center portion, it is also possible that pocket entrances are formed at both right and left portions.

Figure 18:
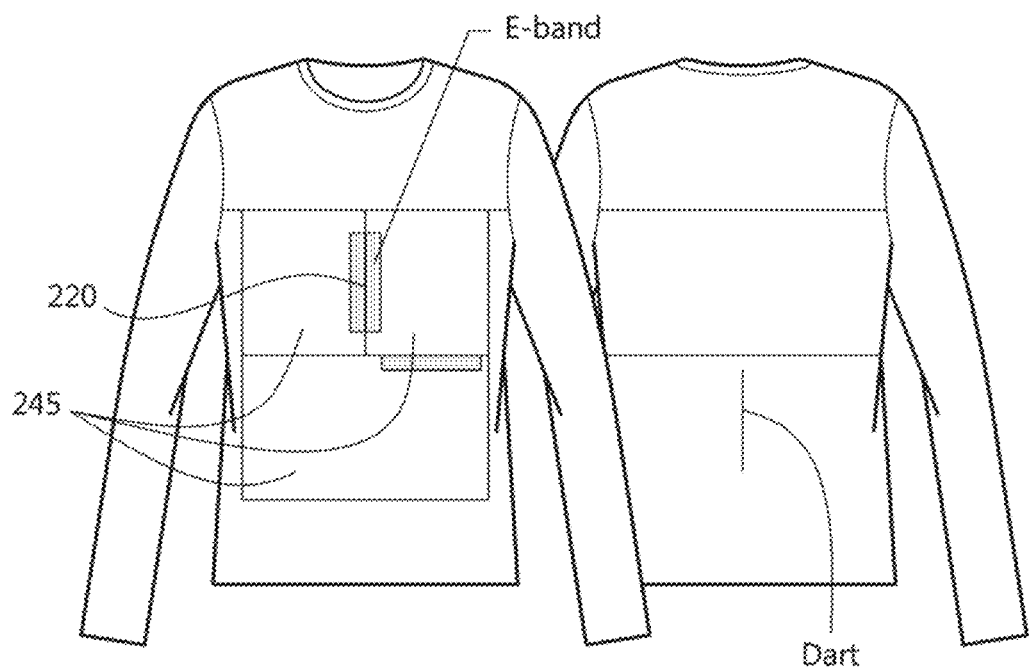
FIG. 18 shows an example of a case in which the clothing to which a textile kit is mounted according to the present disclosure has three electrode-mounting pockets at the front sheet.

FIG. 18 shows an example of a case in which the clothing to which a textile kit is mounted according to the present disclosure has three electrode-mounting pockets at the front sheet. Here, an electrode-mounting pocket 245 is formed at the clothing of Portion (b) of FIG. 13, and two electrode-mounting pockets 245 are provided at the chest portion and one electrode-mounting pocket 245 is provided at the abdominal portion.

FIGS. 17 and 18 may be used for detecting electrocardiogram (ECG) of a mother and electrocardiogram (ECG) of a fetus. In particular, the location of the electrode may be easily adjusted according to a location of the fetus.

Even though FIGS. 16 to 18 depict that the electrode-mounting pocket 245 has a rectangular shape for convenience, the present disclosure is not limited thereto and may have various shapes such an O shape, a rectangular shape, a diamond shape, a triangular shape, a "=" shape, a "≡" shape, a "王" shape, a V shape, an X shape, a radial shape or the like.

Figure 19:
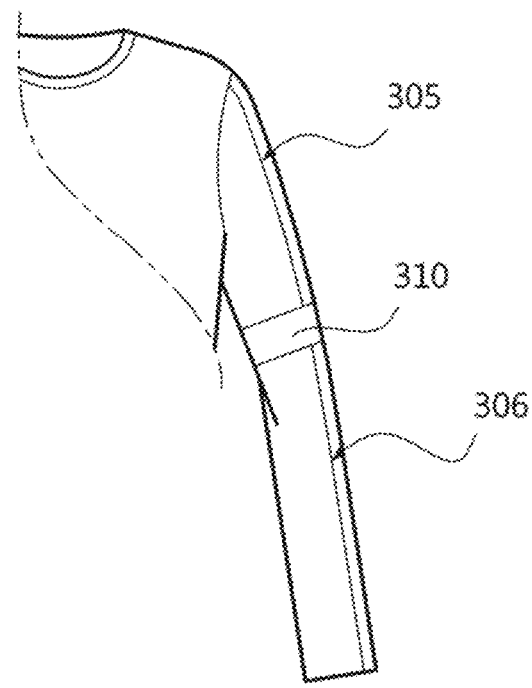
FIG. 19 shows a structure of clothing with a minimized motion artifact, which has an armband-type band according to another embodiment of the present disclosure.

FIG. 19 shows a structure of clothing with a minimized motion artifact, which has an armband-type band according to another embodiment of the present disclosure.

FIG. 19 shows a clothing structure which considers a case where an electrode is mounted, and includes an armband-type band 310, an upper arm vertical band 305 and a lower arm vertical band 306. Portions other than the armband-type band 310, the upper arm vertical band 305 and the lower arm vertical band 306 are made of elastic material.

The armband-type band 310 is made of non-elastic material and has a band shape surrounding an arm portion where an electrode is mounted. The armband-type band 310 has a width varying depending on the size of the electrode and a length corresponding to the arm circumference.

The upper arm vertical band 305 and the lower arm vertical band 306 may be vertical bands installed to form a straight line with the electrode and made of non-elastic material. The upper arm vertical band 305 has a width varying depending on the size of the electrode and a length varying depending on the arm length.

The electromyogram or the like may be detected by using the electrode mounted to the armband-type band 310.

Figure 20:
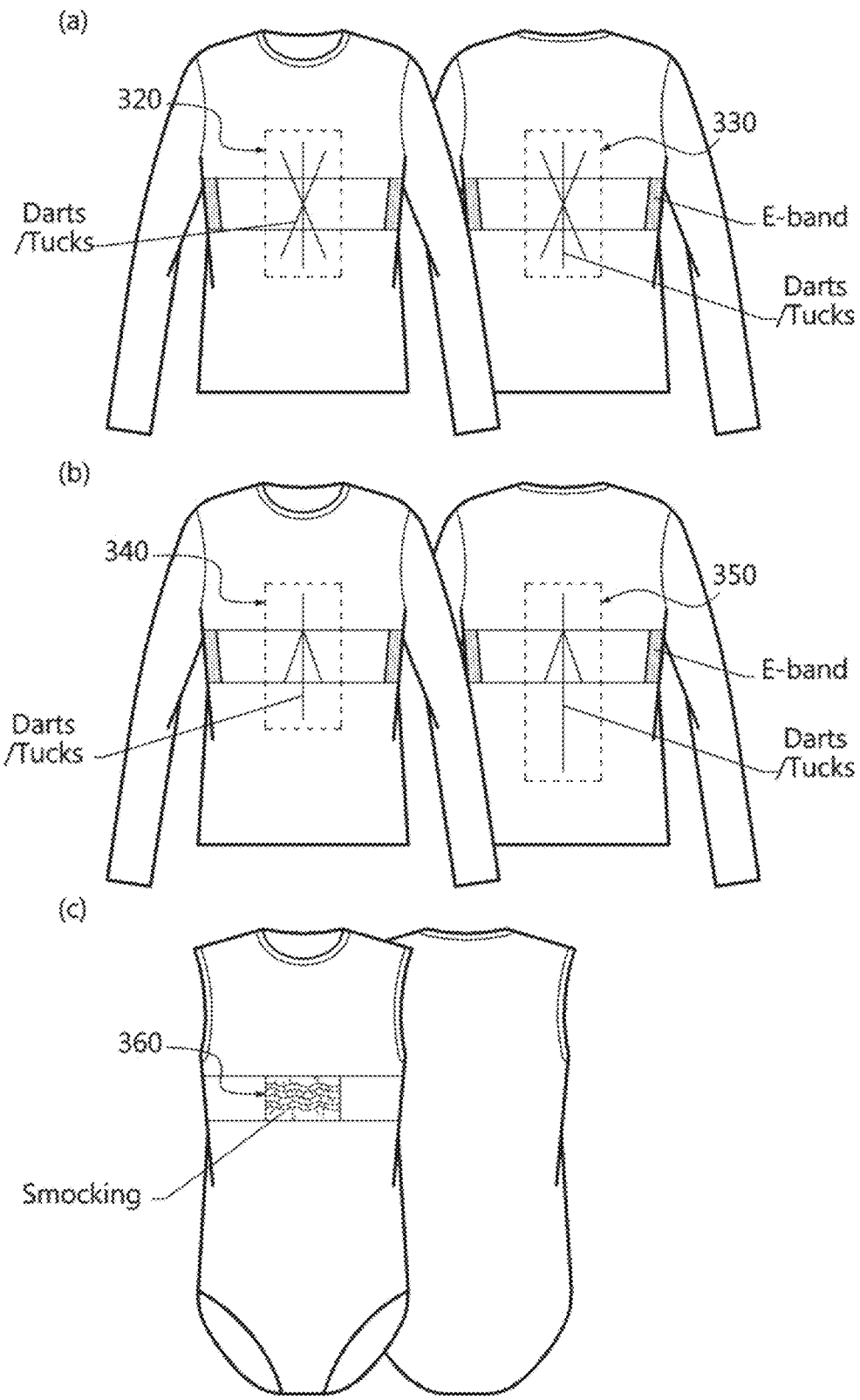
FIG. 20 shows an example of a structure of clothing with a minimized motion artifact, which has various kinds of chest center portions according to the present disclosure, in which Portion (a) of FIG. 20 shows an example of clothing having an asterisk-shaped chest center portion 320 and an asterisk-shaped back center portion 330, Portion (b) of FIG. 20 shows an example of clothing having a Λ-type chest center portion 340 and a Λ-type back center portion 350, and Portion (c) of FIG. 20 shows an example of clothing having a smocking chest center portion 360.

FIG. 20 shows an example of a structure of clothing with a minimized motion artifact, which has various kinds of chest center portions according to the present disclosure.

Portion (a) of FIG. 20 shows an example of clothing having an asterisk-shaped chest center portion 320 and an asterisk-shaped back center portion 330.

An asterisk-shaped (*-shaped) chest center portion 320 has a 1-shaped dart or tuck at the center of the chest and an X-shaped dart or tuck overlapping with the 1-shaped dart or tuck, and is fit to a human body at a concave portion between the chests so that a margin of the clothing does not droop.

The asterisk-shaped back center portion 330 is designed in consideration of a concave portion of the rear sheet along the spine so that the clothing is fit to a human body. The asterisk-shaped back center portion 330 has a 1-shaped dart or tuck at an intermediate portion of the rear sheet and an X-shaped dart or tuck overlapping with the 1-shaped dart or tuck.

Portion (b) of FIG. 20 shows an example of clothing having a Λ-shaped chest center portion 340 and a Λ-shaped back center portion 350.

The Λ-shaped chest center portion 340 has a 1-shaped dart or tuck at the center of the chest and a Λ-shaped dart or tuck at a lower portion of the center of the 1-shaped dart or tuck, so that the 1-shaped dart or tuck overlaps with the Λ-shaped dart or tuck. By doing so, a margin of the clothing does not droop at a concave portion between the chests but is fit to a human body.

The Λ-shaped back center portion 350 is designed in consideration of a concave portion of the rear sheet along the spine so that the clothing is fit to a human body. The Λ-shaped back center portion 350 has a 1-shaped dart or tuck at an intermediate portion of the rear sheet and a Λ-shaped dart or tuck at a lower portion of the center of the 1-shaped dart or tuck, so that the 1-shaped dart or tuck overlaps with the Λ-shaped dart or tuck.

Portion (c) of FIG. 20 shows an example of clothing having a smocking chest center portion 360.

The smocking chest center portion 360 has a smocking portion between the chests so that a margin of the clothing does not droop at a concave portion between the chests but is fit to a human body.

Figure 21:
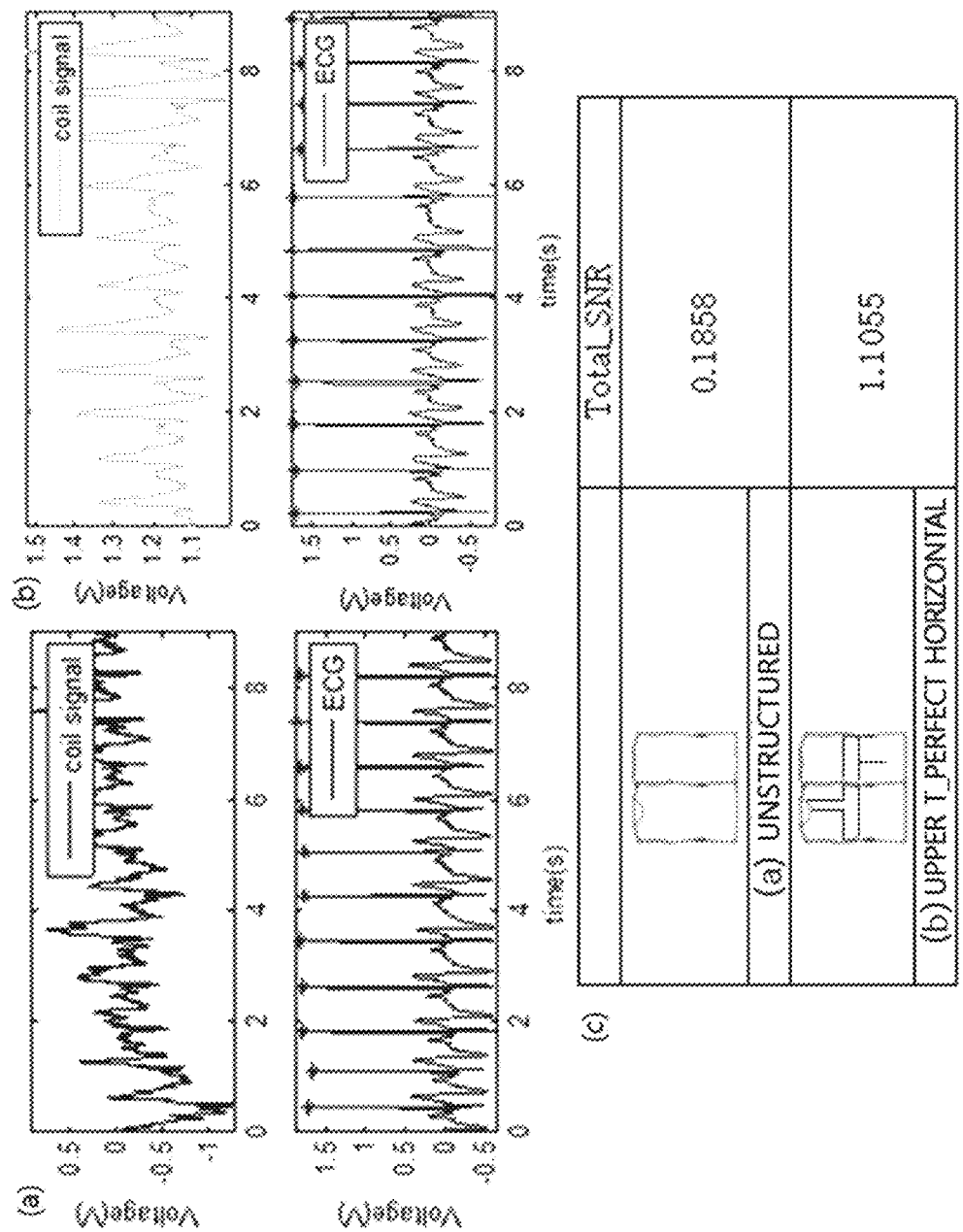
FIG. 21 shows an example of comparison results of the degree of a motion artifact decrease, obtained by detecting a heart activity signal from the clothing with a minimized motion artifact according to the present disclosure and general clothing.

FIG. 21 shows an example of comparison results of the degree of a motion artifact decrease, obtained by detecting a heart activity signal from the clothing with a minimized motion artifact according to the present disclosure and general clothing. When a single person wears two kinds of clothing alternately and performs motions, a heart activity signal is detected.

Portion (a) of FIG. 21 shows an example in which a non-contact electrode is mounted to general clothing, which does not include the front center band 211, the back center band 231 and the first vertical support unit 205, to detect a heart activity signal. An upper portion of Portion (a) of FIG. 21 shows a heart activity signal detected by the non-contact electrode mounted to general clothing, and in a lower portion of Portion (a) of FIG. 21, an electrocardiogram (ECG) signal is detected as a reference signal by means of an existing electrocardiogram (ECG) detection method in order to check whether the heart activity signal is detected properly.

Portion (b) of FIG. 21 shows an example in which a non-contact electrode is mounted to the clothing, which includes the front center band 211, the back center band 231 and the first vertical support unit 205 in order to minimize a motion artifact according to the present disclosure, to detect a heart activity signal. An upper portion of Portion (b) of FIG. 21 shows a heart activity signal detected by the non-contact electrode mounted to the clothing having a minimized motion artifact according to the present disclosure, and in a lower portion of Portion (b) of FIG. 21, an electrocardiogram (ECG) signal is detected as a reference signal by means of an existing electrocardiogram (ECG) detection method in order to check whether the heart activity signal is detected properly.

It can be understood that an upper graph of Portion (b) of FIG. 21, namely the heart activity signal detected by the non-contact electrode mounted to the clothing having a minimized motion artifact according to the present disclosure, has a greatly reduced artifact in comparison to an upper graph of Portion (a) of FIG. 21, namely the heart activity signal detected by the electrode mounted to general clothing.

Portion (c) of FIG. 21 shows an example of a signal-to-artifact ratio (SNR) obtained by using the result of the upper portion of Portion (b) of FIG. 21 and the result of the upper portion of Portion (a) of FIG. 21, the result of the upper portion of Portion (b) of FIG. 21, namely the heart activity signal detected by the non-contact electrode mounted to the clothing having a minimized motion artifact according to the present disclosure, has a greater signal-to-artifact ratio.

In other words, from the above, it can be understood that a motion artifact may be greatly reduced by using the clothing having a minimized motion artifact according to the present disclosure.

Though the present disclosure has been described with the limited embodiments and drawings, the present disclosure is not limited to these embodiments, and various changes and modifications can be made thereto from the disclosure by those having ordinary skill in the art. Therefore, the scope of the present disclosure should be defined based on the appended claims, and its modifications and equivalents should also be regarded as falling into the scope of the present disclosure.

| Reference Symbols |
|---|
| 10: textile electrode kit |
| 110: electrode |
| 113: non-contact electrode |
| 115: spiral coil |
| 130: signal detection module |
| 133: signal pre-processing unit |
| 137: transmitting unit |
| 139: electrode driving unit |
| 140: three-dimensional structure |
| 147: discontinuous space |
| 170: upper cover member |
| 175: coil-mounted textile sheet |
| 185: clothing electrode mounting portion |
| 190: sewing |
| 194: top surface |
| 195: bottom surface |
| 196: left side surface |
| 197: right side surface |
| 205: first vertical support unit |
| 206: second vertical support unit |
| 209: front lower end |
| 210: chest tunnel |
| 211: front center band |
| 213: left chest tunnel |
| 214: right chest tunnel |
| 215: left front center band |
| 216: right front center band |
| 219: chest center elastic member |

| Reference Symbols -continued |
|---|
| 220: central entrance |
| 221: elastic member |
| 221a: under-armpit elastic member |
| 221b: under-chest elastic member |
| 222: side entrance |
| 227: front upper central dart |
| 228: back lower central dart |
| 229: waste sideline elastic member |
| 230: back center tunnel |
| 231: back center band |
| 240: abdominal tunnel |
| 241: front abdominal band |
| 250: rectangular non-elastic unit |
| 251: rectangular cut line |
| 252: in-square horizontal support unit |
| 253: in-square upper vertical support unit |
| 254: in-square lower vertical support unit |
| 271: quadrant I |
| 272: quadrant II |
| 273: quadrant III |
| 274: quadrant IV |
| 275: in-square lower support unit |
| 281: back abdominal band |
| 305: upper arm vertical band |
| 306: lower arm vertical band |
| 310: armband-type band |
| 320: asterisk-shaped chest center portion |
| 330: asterisk-shaped back center portion |
| 340: Λ-shaped chest center portion |
| 350: Λ-shaped back center portion |
| 360: smocking chest center portion |
| 410: sleeve portion |
| 420: neck girth |

What is claimed is:

1. A clothing for detecting a bio-signal, comprising:
right and left elastic members respectively located below right and left under-armpits or right and left chests;
a front center band comprising:
a chest center elastic member located at a center of the front center band;
a left front center band made of a non-elastic material, one end of the left front center band being mounted to one end of the left elastic member, the other end of the left front center band being mounted to one end of the chest center elastic member; and
a right front center band made of a non-elastic material, one end of the right front center band being mounted to one end of the right elastic member, the other end of the right front center band being mounted to the other end of the chest center elastic member;
a back center band made of a non-elastic material with a band shape and located at a rear sheet of the clothing, one end of the back center band being mounted to the other end of the left elastic member, the other end of the back center band being mounted to the other end of the right elastic member;
a back lower central dart vertically extending from a center of a lower end of the back center band to a waist portion, so that the clothing forms a three-dimensional shape having a concave portion between the lower end of the back center band and the waist portion that is configured to conform to a lower spinal curvature of a wearer;
a front upper central dart vertically extending from a neckline center of center elastic member, so that the clothing forms a three-dimensional shape of a chest surface that is configured to conform to a cleavage and breasts of the wearer; and a textile electrode kit mounted to at least one of the front center band and the back center band.

2. The clothing according to claim 1, wherein at least one of the front center band and the back center band is disposed at an inner side of the clothing which is configured to contact the skin of the wearer.

3. The clothing according to claim 1, wherein a sleeve portion connecting shoulders and arms of the clothing is formed with a mesh structure, a slit structure, a cut-out structure, a folding structure or a pleat structure.

4. The clothing according to claim 1, wherein a neck girth of the clothing is formed with a mesh structure, a slit structure, a cut-out structure, a folding structure or a pleat structure.

5. The clothing according to claim 1, wherein the textile electrode kit includes:
   an electrode having a surface electrode and configured to contact the skin of the wearer to detect the bio signal;
   a lower fixed member having one surface to which the electrode is mounted;
   a three-dimensional structure mounted to the other surface of the lower fixed member;
   a signal detection module located on the three-dimensional structure and mounted in a housing and configured to amplify the bio signal received from the electrode and remove artifact therefrom; and
   an upper cover member configured to surround the signal detection module and having a rim which is sewed or attached together with a rim of the lower fixed member.

6. The clothing according to claim 1, wherein the textile electrode kit includes:
   an electrode having a spiral coil formed on a coil-mounted textile sheet to receive an oscillation signal from an oscillation circuit and output the oscillation signal including the bio signal;
   a three-dimensional structure located on the electrode;
   a signal detection module located on the three-dimensional structure and mounted in a housing, the signal detection module including an electrode driving unit which has the oscillation circuit to output the oscillation signal, the signal detection module is configured to detect the oscillation signal which includes the bio signal from the electrode and amplify the detected bio signal and removing artifact therefrom; and
   an upper cover member configured to surround the signal detection module and having a rim which is sewed or attached together with a rim of the coil-mounted textile sheet or sewed or attached together with of a lower fixed member located below the electrode.

7. The clothing according to claim 1, wherein the textile electrode kit includes:
   an electrode having a spiral coil formed on a coil-mounted textile sheet to receive an oscillation signal from an oscillation circuit and output the oscillation signal including the bio signal;
   a three-dimensional structure located above a lower fixed member and below the electrode; and
   an upper cover member configured to surround the electrode and having a rim which is sewed or attached together with a rim of the lower fixed member.

8. The clothing according to claim 1, wherein the textile electrode kit includes:
   an electrode having a spiral coil formed on a coil-mounted textile sheet to receive an oscillation signal from an oscillation circuit and output the oscillation signal including the bio signal;
   a three-dimensional structure located below the electrode; and
   a lower fixed member having one surface to which the three-dimensional structure is mounted, the lower fixed member having a rim which is sewed together with a rim of the coil-mounted textile sheet.

* * * * *